US010035956B2

(12) United States Patent
Chin et al.

(10) Patent No.: US 10,035,956 B2
(45) Date of Patent: Jul. 31, 2018

(54) COMPOUND AND LIQUID-CRYSTAL COMPOSITION EMPLOYING THE SAME

(71) Applicant: INDUSTRIAL TECHNOLOGY RESEARCH INSTITUTE, Hsinchu (TW)

(72) Inventors: Chih-Lung Chin, Hsinchu (TW); Chien-Hsien Cheng, Tainan (TW); Chao-Wu Liaw, Xiluo Township (TW); Shih-Hsien Liu, Jhubei (TW); Kung-Lung Cheng, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 164 days.

(21) Appl. No.: 15/333,583

(22) Filed: Oct. 25, 2016

(65) Prior Publication Data

US 2017/0174995 A1  Jun. 22, 2017

Related U.S. Application Data

(63) Continuation-in-part of application No. 14/976,947, filed on Dec. 21, 2015.

(51) Int. Cl.
*C09K 19/58*       (2006.01)
*C07C 69/96*       (2006.01)
(Continued)

(52) U.S. Cl.
CPC ............ *C09K 19/586* (2013.01); *C07C 69/76* (2013.01); *C07C 69/96* (2013.01); *C07D 407/12* (2013.01);
(Continued)

(58) Field of Classification Search
CPC .... C09K 19/32; C09K 19/542; C09K 19/586; C08F 22/10; C07C 69/76; C07C 69/96
See application file for complete search history.

(56) References Cited

U.S. PATENT DOCUMENTS

| | | |
|---|---|---|
| 622,056 A | 3/1899 | Marshall |
| 3,945,968 A | 3/1976 | Goletto |

(Continued)

FOREIGN PATENT DOCUMENTS

| | | |
|---|---|---|
| TW | I271431IB | 1/2007 |
| TW | 201245422 A1 | 11/2012 |

(Continued)

OTHER PUBLICATIONS

Hsieh et al., "Preparation and Characterization of Polymer Stabilized Liquid Crystal cells with Chiral compounds derived from Camphor," 2007 International Symposium on Nano Science and Technology, Tainan, Taiwan, Nov. 8-9, 2007, 2 pages.

(Continued)

*Primary Examiner* — Cynthia H Kelly
*Assistant Examiner* — Anna Malloy
(74) *Attorney, Agent, or Firm* — Birch, Stewart, Kolasch & Birch, LLP

(57) ABSTRACT

A compound and a liquid-crystal composition employing the same are provided. The compound has a structure represented by Formula (I)

$$B^2-R^2-Z^4-A^4-Z^2-A^2-Z^b\diagup(R)_3$$
$$(R)_3\diagdown Z^a-A^1-Z^1-A^3-Z^3-R^1-B^1$$

wherein $Z^a$ and $Z^b$ are independently $$-\!\!\left(\!\!\begin{array}{c}O\\\|\\C-O\end{array}\!\!\right)\!\!-, -\!\!\left(\!\!\begin{array}{c}O\\\|\\O-C-O\end{array}\!\!\right)\!\!-, -\!\!\left(\!\!\begin{array}{c}O\\\|\\C-N\\\;\;H\end{array}\!\!\right)\!\!-,$$

$$-\!\!\left(\!\!\begin{array}{c}O\\\|\\N-C\\H\end{array}\!\!\right)\!\!-, -\!\!\left(\!\!\begin{array}{c}O\\\|\\C-S\end{array}\!\!\right)\!\!-, \text{or} -\!\!\left(\!\!\begin{array}{c}O\\\|\\S-C\end{array}\!\!\right)\!\!-;$$

$A^1$, $A^2$, $A^3$ and $A^4$ are independently single bond, (ring structures with O, S, benzene, $(R)_4$ substituted, naphthalene groups), or $Z^1$, $Z^2$, $Z^3$, and $Z^4$ are independently single bond, (Continued)

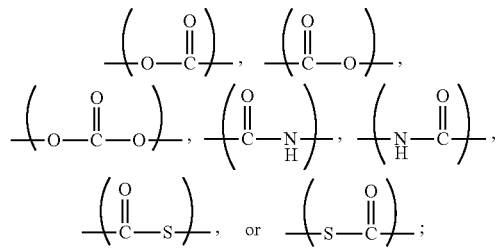

R is independently hydrogen, or $C_{1-4}$ alkyl group; $R^1$ and $R^2$ are independently single bond, $-O-(CH_2)_n-$, $-CH=CH-(CH_2)_2-$, $-(CH_2)_2-CH=CH-$, $-CH=CH-$, or $-C\equiv C-$; n is an integer from 1 to 6; $B^1$ and $B^2$ are independently

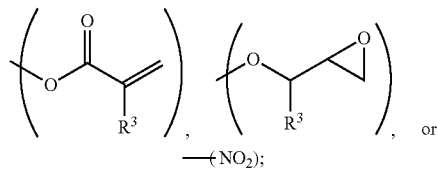

and, $R^3$ is hydrogen, or methyl group.

10 Claims, No Drawings

(51) Int. Cl.
| | |
|---|---|
| C08F 22/10 | (2006.01) |
| C07C 69/76 | (2006.01) |
| C07D 407/12 | (2006.01) |
| C07D 409/12 | (2006.01) |
| C09K 19/32 | (2006.01) |
| C09K 19/04 | (2006.01) |

(52) U.S. Cl.
CPC ............ *C07D 409/12* (2013.01); *C08F 22/10* (2013.01); *C09K 19/32* (2013.01); *C07C 2101/14* (2013.01); *C07C 2103/94* (2013.01); *C07C 2601/14* (2017.05); *C07C 2603/94* (2017.05); *C09K 2019/0448* (2013.01)

(56) References Cited

U.S. PATENT DOCUMENTS

| 4,346,167 | A | 8/1982 | Imatomi et al. |
|---|---|---|---|
| 4,895,793 | A | 1/1990 | Seto et al. |
| 5,024,850 | A | 6/1991 | Broer et al. |
| 5,053,555 | A | 10/1991 | Yeager et al. |
| 5,744,057 | A | 4/1998 | Meyer et al. |
| 7,052,743 | B2 | 5/2006 | Welter et al. |
| 7,150,900 | B2 | 12/2006 | Welter |
| 7,329,368 | B2 | 2/2008 | Welter |
| 7,452,482 | B2 | 11/2008 | Welter |
| 7,470,376 | B2 | 12/2008 | Welter et al. |
| 7,820,251 | B2 | 10/2010 | Chen et al. |
| 8,023,080 | B2 | 9/2011 | Kuo et al. |
| 8,449,953 | B2 | 5/2013 | Cheng et al. |
| 8,460,766 | B2 | 6/2013 | Huang et al. |
| 8,715,528 | B2 | 5/2014 | Chen et al. |
| 8,906,472 | B2 | 12/2014 | Kuriyama et al. |
| 2005/0072961 | A1 | 4/2005 | Welter et al. |
| 2012/0289731 | A1 | 11/2012 | Chen et al. |
| 2014/0022473 | A1 | 1/2014 | Goetz et al. |
| 2014/0256896 | A1 | 9/2014 | Nakata et al. |

FOREIGN PATENT DOCUMENTS

| TW | I410424 | B | 10/2013 |
|---|---|---|---|
| TW | I414527 | B | 11/2013 |
| TW | I443180 | B | 7/2014 |
| TW | I480635 | B | 4/2015 |

OTHER PUBLICATIONS

Sen et al, "Spiro-biindane containing fluorinated poly(ether imide)s: Synthesis, characterization and gas separation properties," Journal of Membrane Science, vol. 365, 2010, (Available Online Sep. 25, 2010), pp. 329-340.

Stenzel et al., "Bis(2,4,7-trimethylindenyl)cobalt(II) and rac-2,2',4,4',7,7'-hexamethyl-1,1'-biindene," Acta Crystallographica, Section C, C57, 2001, pp. 1056-1059.

Taiwanese Office Action and Search Report for Taiwanese Application No. 104143092, dated Jul. 22, 2016.

COMPOUND AND LIQUID-CRYSTAL COMPOSITION EMPLOYING THE SAME

CROSS REFERENCE TO RELATED APPLICATIONS

This application is a Continuation-In-Part of pending U.S. patent application Ser. No. 14/976,947, filed Dec. 21, 2015 and entitled "compound and liquid-crystal composition employing the same", the entirety of which is incorporated by reference herein.

TECHNICAL FIELD

The disclosure relates to a compound and a liquid-crystal composition employing the same.

BACKGROUND

In recent years, compounds having a terminal reactive functional group are generally used in the elements (such as a liquid-crystal composition or an optical film) of a liquid-crystal display. For example, a compound having a terminal reactive functional group may be employed in the manufacture of a cholesteric liquid-crystal composition, a brightness enhancement film, or an alignment film. Due to the different chemical structures, conventional compounds having a terminal reactive functional group, however, have low solubility in the liquid-crystal host, resulting in a poor film-forming ability being exhibited by liquid-crystal compositions that employ conventional compounds with a terminal reactive functional group.

SUMMARY

An embodiment of the disclosure provides a compound, wherein the compound has a structure represented by Formula (I):

Formula (I)

$$B^2-R^2-Z^4-A^4-Z^2-A^2-Z^b \cdots (R)_3$$
$$(R)_3 \cdots Z^a-A^1-Z^1-A^3-Z^3-R^1-B^1$$

wherein $Z^a$ and $Z^b$ are independently

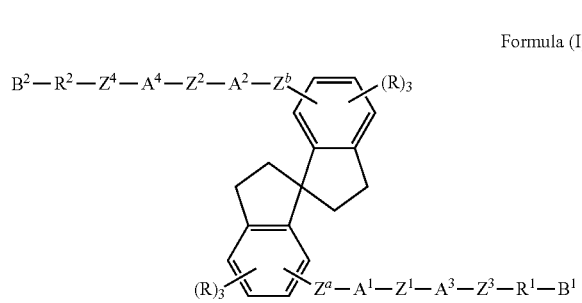

$A^1$ and $A^2$ are independently (structures shown: furan, thiophene, phenylene with $(R)_4$, cyclohexylene with $(R)_4$, naphthalene, or naphthalene);

$A^3$ and $A^4$ are independently single bond, (structures shown: furan, thiophene, phenylene with $(R)_4$, cyclohexylene with $(R)_4$, naphthalene, or naphthalene);

$Z^1$, $Z^2$, $Z^3$, and $Z^4$ are independently single bond, (structures shown: $-O-C(=O)-$, $-C(=O)-O-$, $-O-C(=O)-O-$, $-C(=O)-NH-$, $-NH-C(=O)-$, $-C(=O)-S-$, or $-S-C(=O)-$);

R is independently hydrogen, or $C_{1-4}$ alkyl group; $R^1$ and $R^2$ are independently single bond, $-O-(CH_2)_n-$, $-CH=CH-(CH_2)_2-$, $-(CH_2)_2-CH=CH-$, $-CH=CH-$, or $-C\equiv C-$; n is an integer from 1 to 6; $B^1$ and $B^2$ are independently

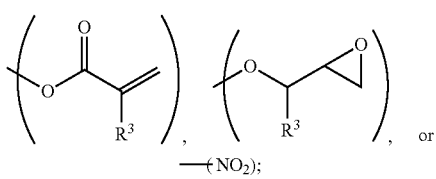

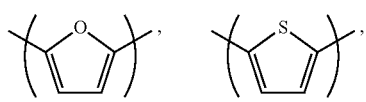

and, $R^3$ is hydrogen, or methyl group.

According to another embodiment of the disclosure, the disclosure also provides a liquid-crystal composition including 100 parts by weight of liquid-crystal host; and 0.1-30 parts by weight of the aforementioned compound.

DETAILED DESCRIPTION

The disclosure provides a compound and a liquid-crystal composition employing the same. Due to the specific chemical structure, the compound of the disclosure exhibits high helical twisting power (HTP), high solubility in the liquid-crystal host, stable temperature dependence, narrow wavelength variation range, and accurately adjusts the reflective wavelength of cholesteric liquid-crystal, and enhances the stability of cholesteric liquid-crystal. Therefore, the cholesteric liquid-crystal employing the compound has wide application.

According to embodiments of the disclosure, the compound of the disclosure can have a structure of Formula (I):

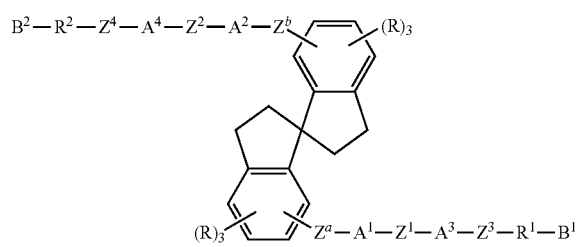

Formula (I)

wherein $Z^a$ and $Z^b$ are independently

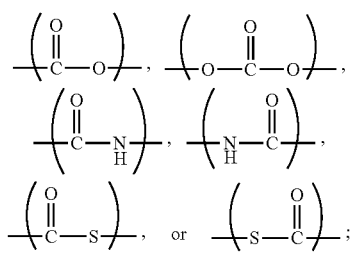

$A^1$ and $A^2$ are independently

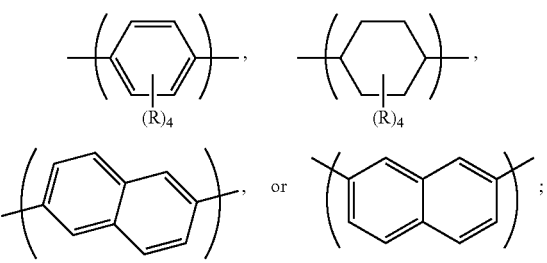

$A^3$ and $A^4$ are independently single bond,

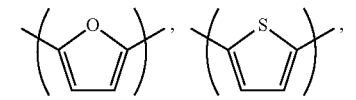

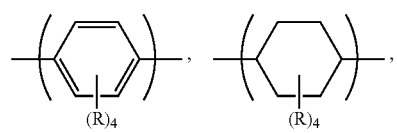

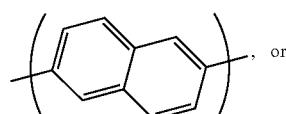

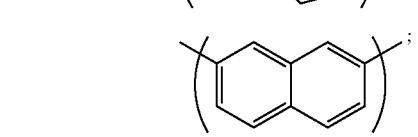

$Z^1$, $Z^2$, $Z^3$, and $Z^4$ are independently single bond,

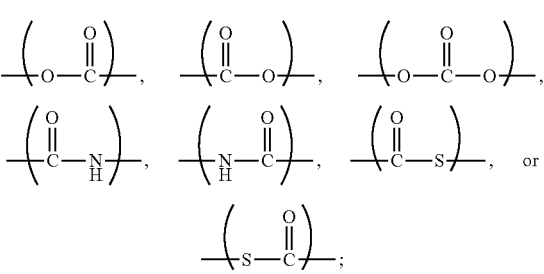

R is independently hydrogen, or $C_{1-4}$ alkyl group; $R^1$ and $R^2$ are independently single bond, —O—$(CH_2)_n$—, —CH=CH—$(CH_2)_2$—, —$(CH_2)_2$—CH=CH—, —CH=CH—, or —C≡C—; n is an integer from 1 to 6; $B^1$ and $B^2$ are independently

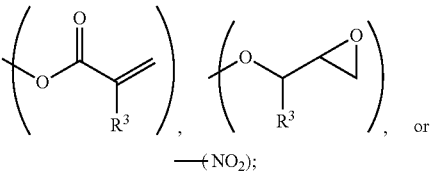

and, $R^3$ is hydrogen, or methyl group. The biindane moiety of the compound represented by Formula (I) can be S-form or R-form.

According to embodiments of the disclosure, the compound of the disclosure can have a carbonate ester moiety for bonding a side chain. For example, the compound can have a structure of Formula (II)

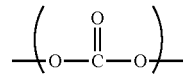

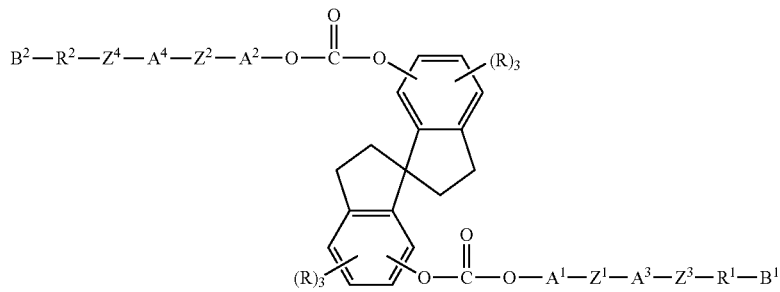

Formula (II)

wherein $A^1$, $A^2$, $A^3$, $A^4$, $Z^1$, $Z^2$, $Z^3$, $Z^4$R, $R^1$, $R^2$, $B^1$, and $B^2$ are as previously defined. For example, the compound can be

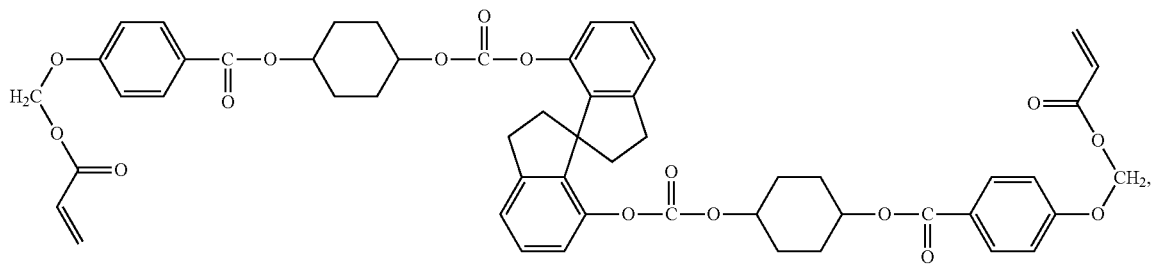

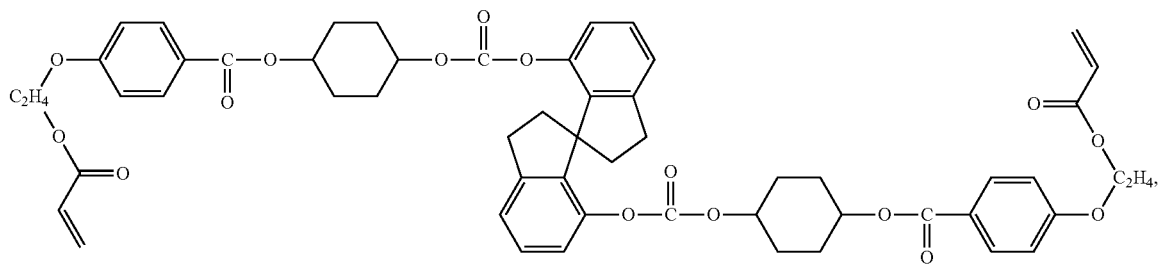

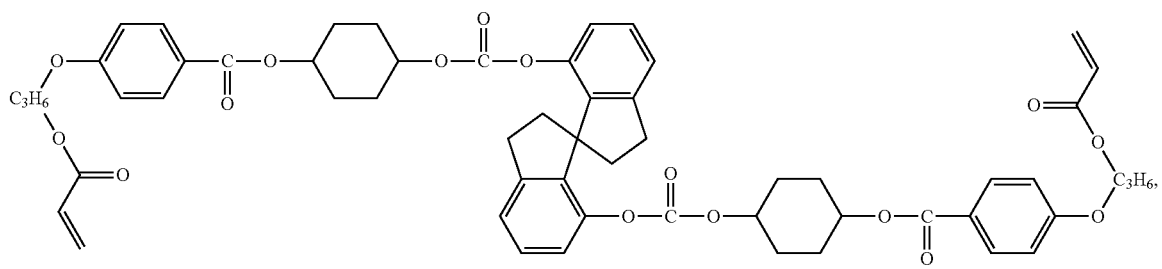

-continued
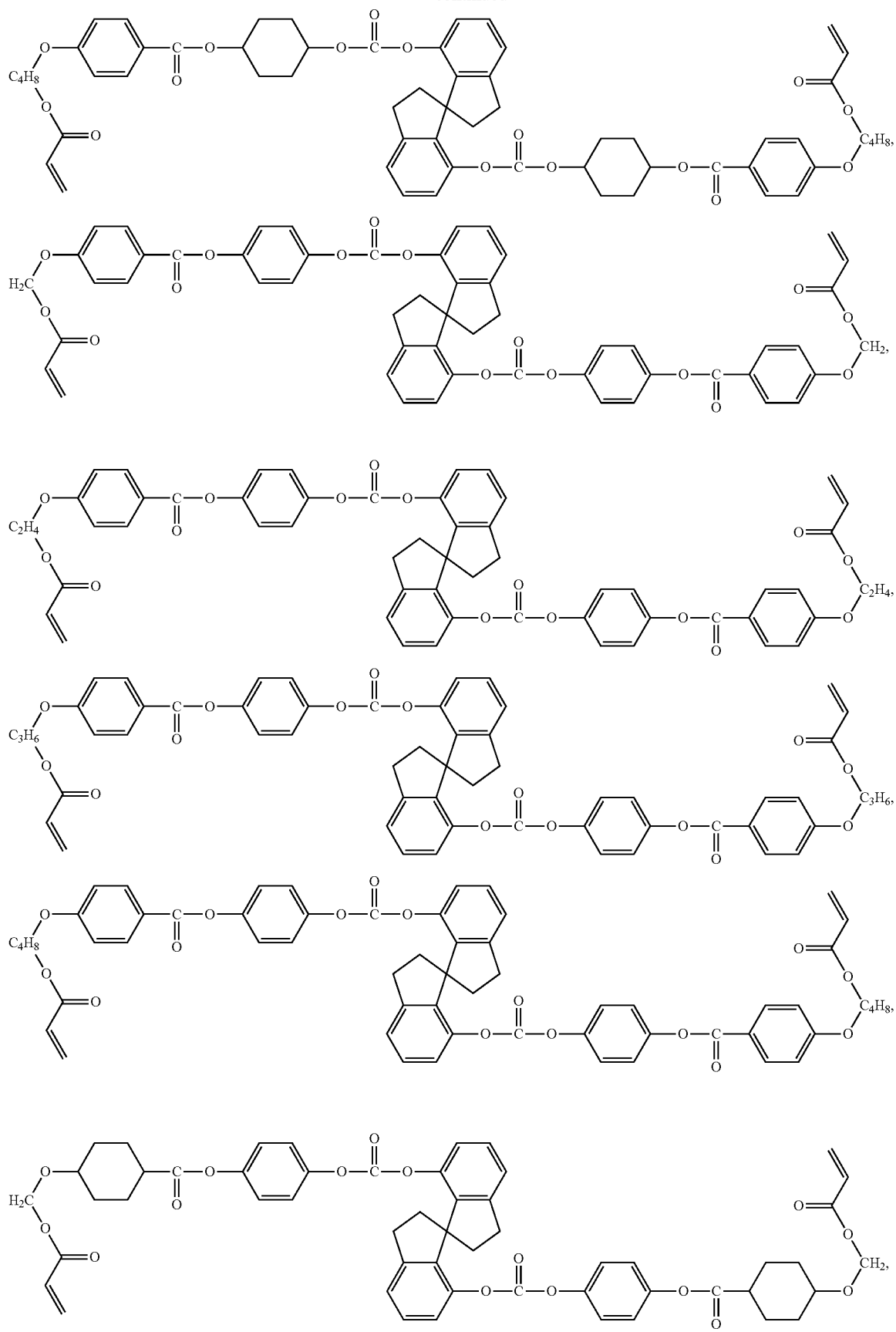

-continued
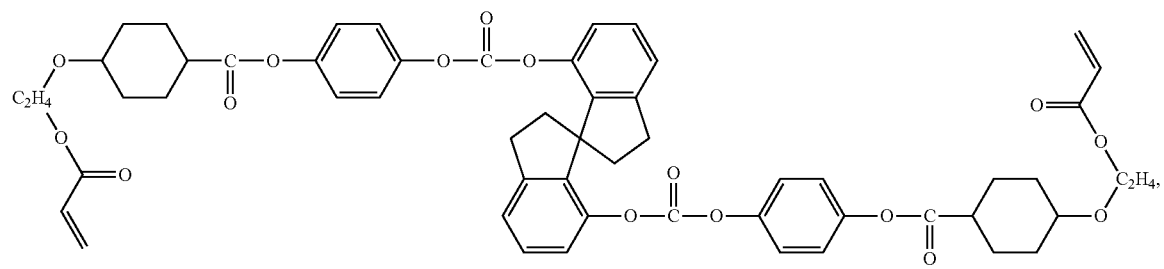
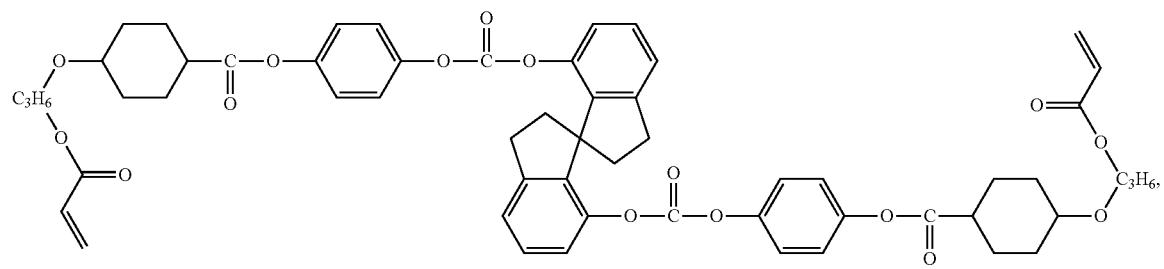
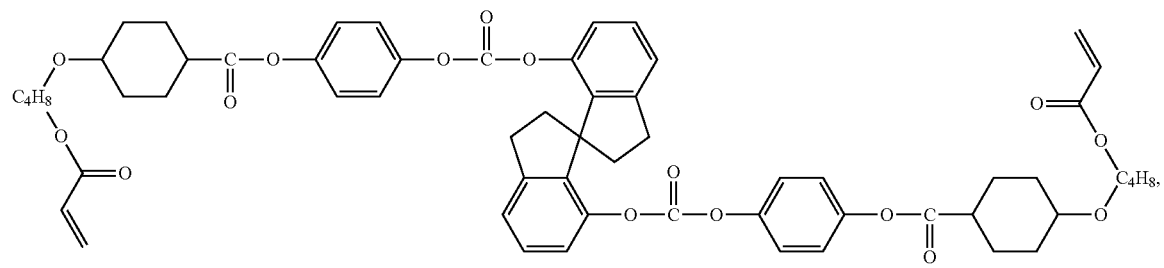
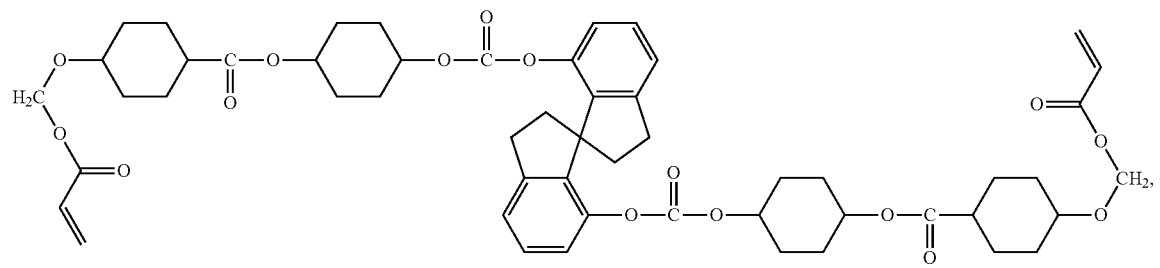
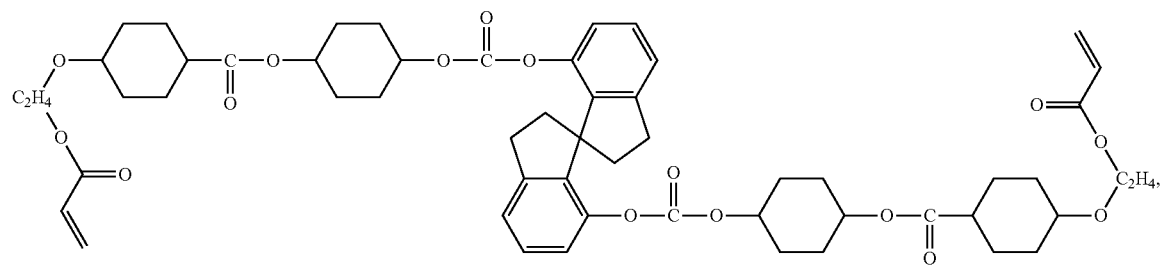
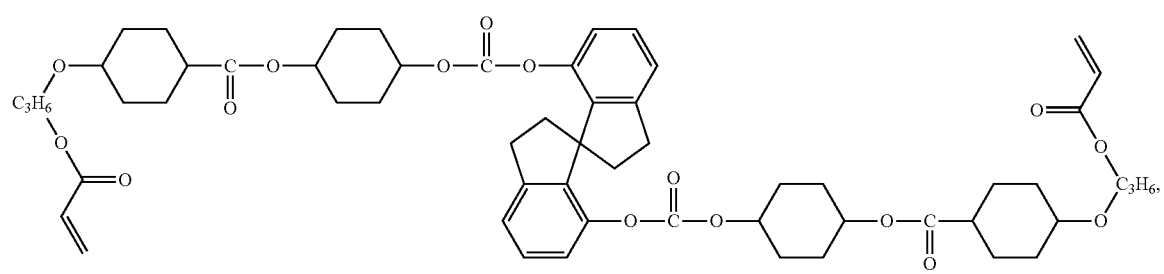

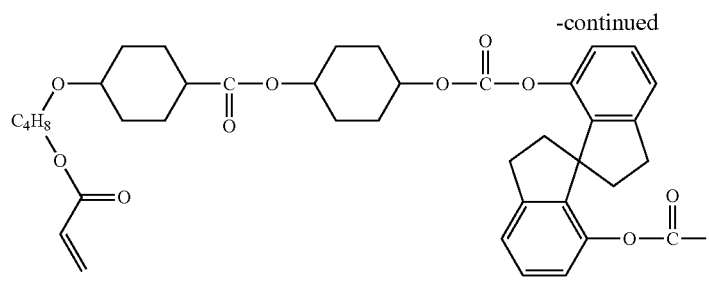
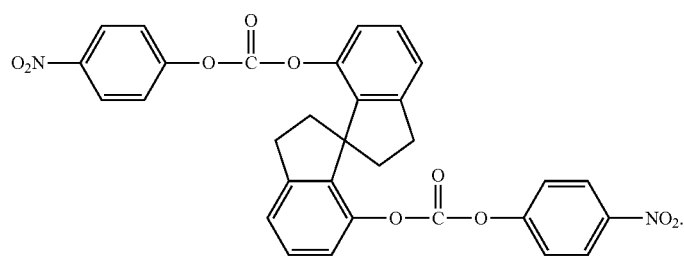
The biindane moiety of the compound represented by Formula (II) can be S-form or R-form.
According to embodiments of the disclosure, the compound of the disclosure can have a structure of Formula (III):
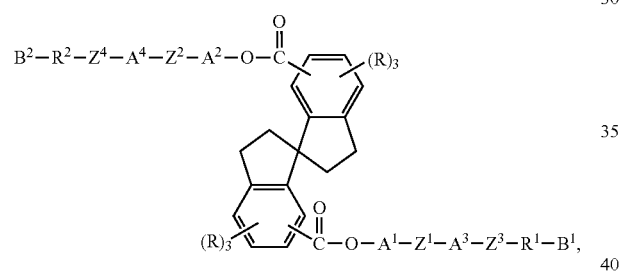
Formula (III)
wherein $A^1$, $A^2$, $A^3$, $A^4$, $Z^1$, $Z^2$, $Z^3$, $Z^4$, R, $R^1$, $R^2$, $B^1$, and $B^2$ are as previously defined. For example, the compound can be
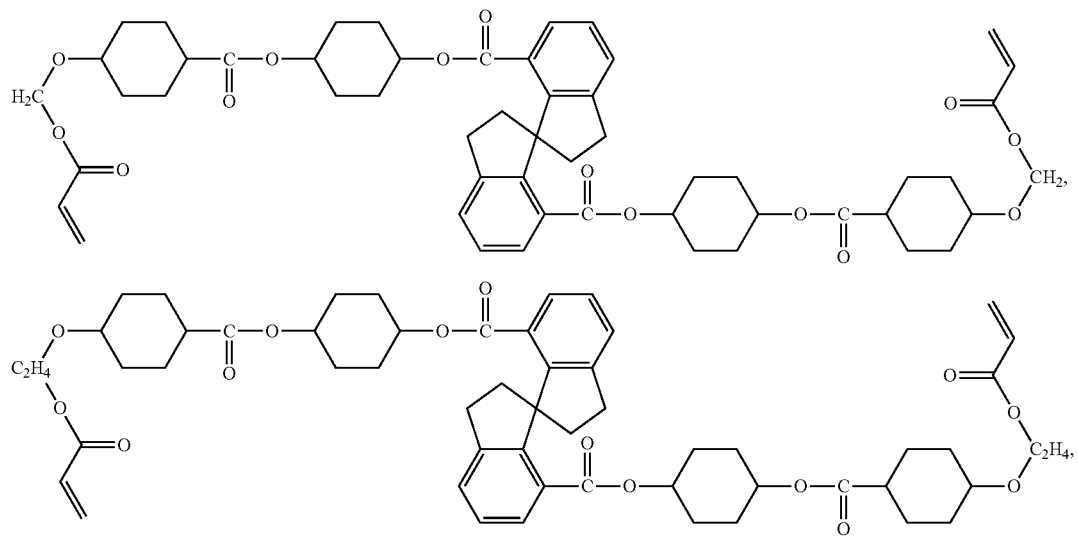

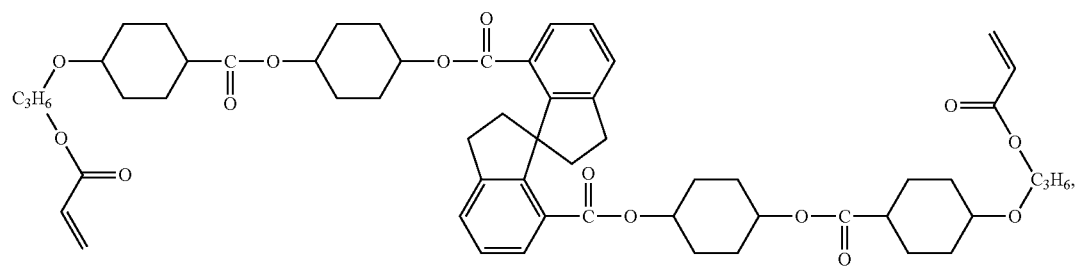
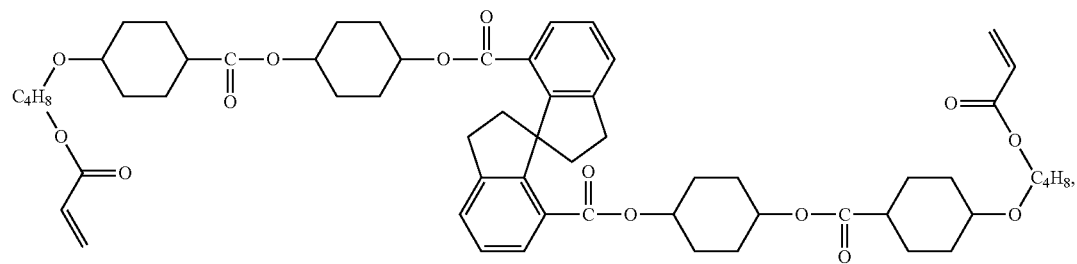
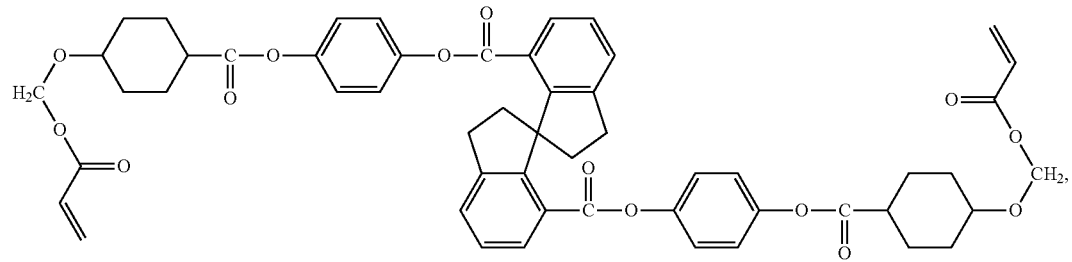
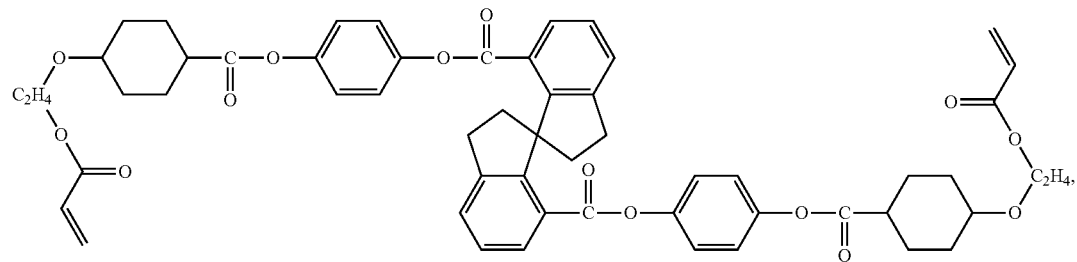
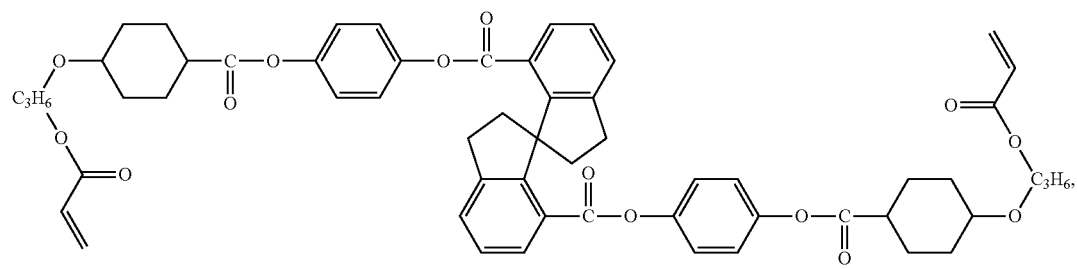
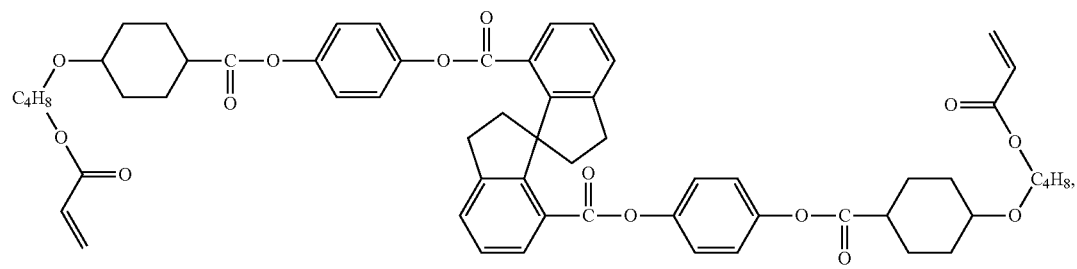

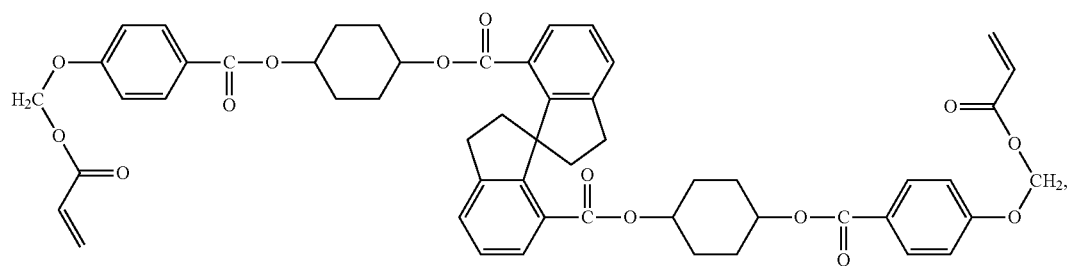
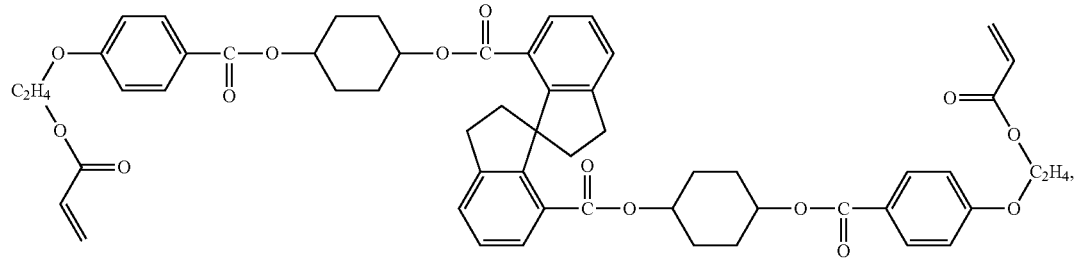
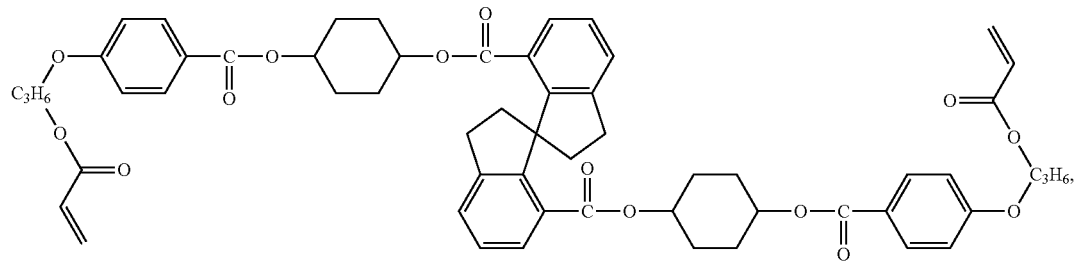
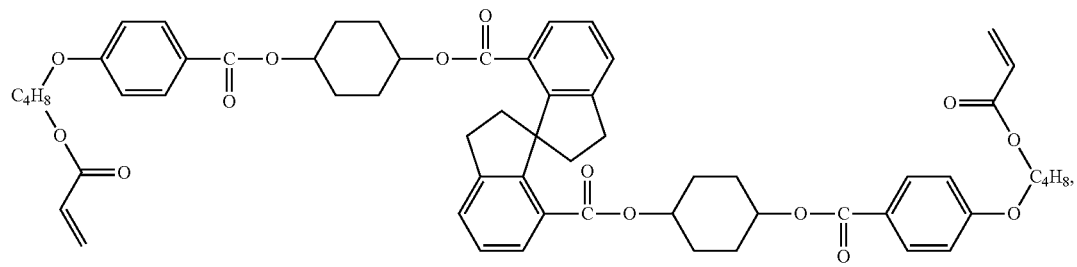
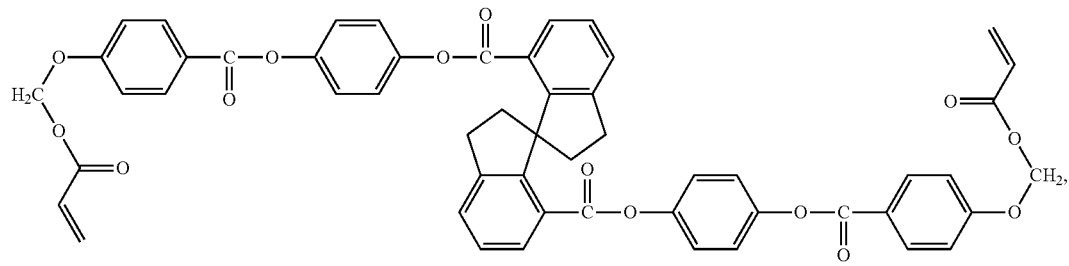
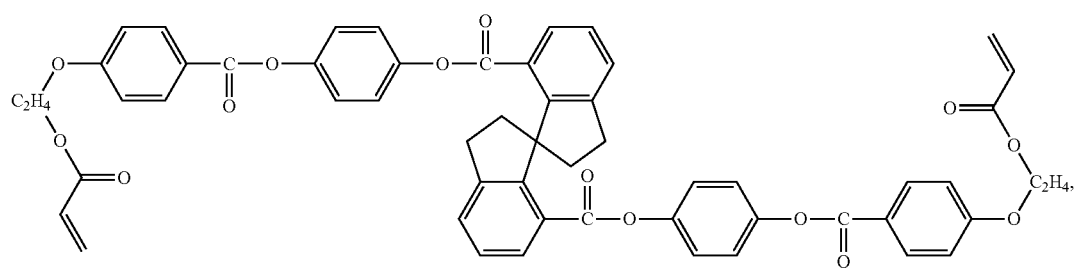

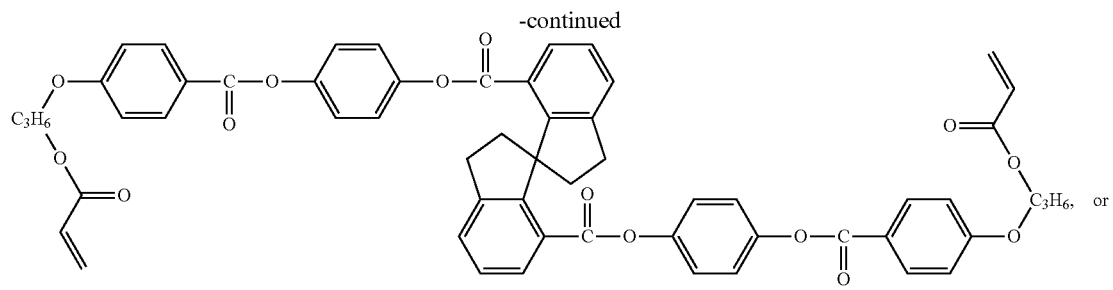
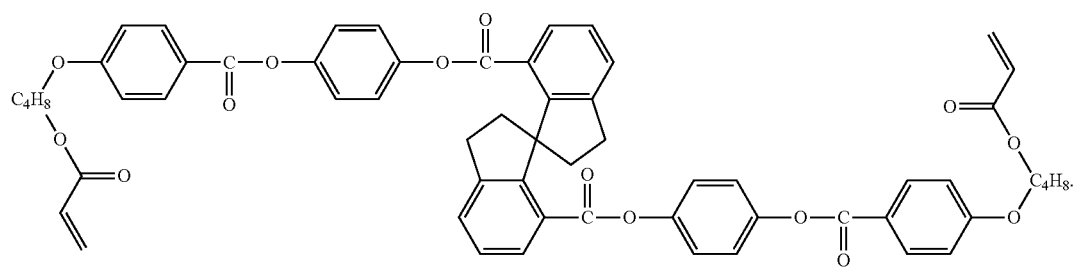
The biindane moiety of the compound represented by Formula (III) can be S-form or R-form.
According to embodiments of the disclosure, the compound of the disclosure can have a structure of Formula (IV) or (V):
Formula (IV)
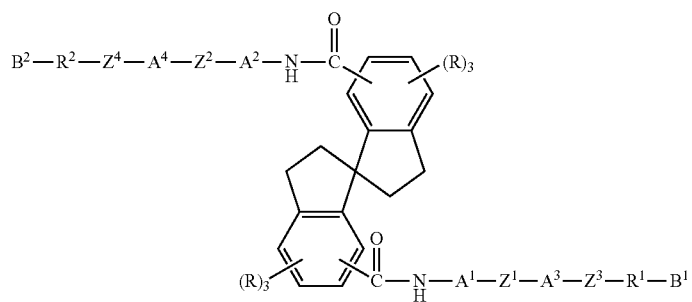
Formula (V)
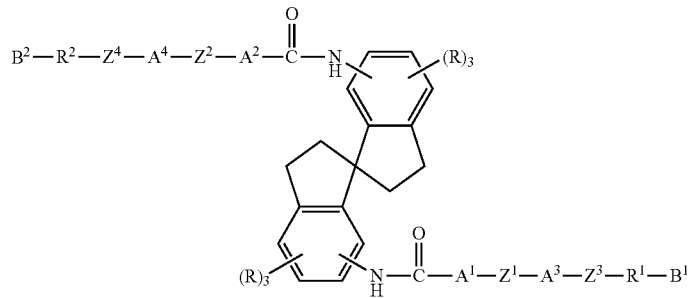
wherein $A^1, A^2, A^3, A^4, Z^1, Z^2 Z^3, Z^4, R, R^1, R^2, B^1$, and $B^2$ are as previously defined. For example, the compound can be

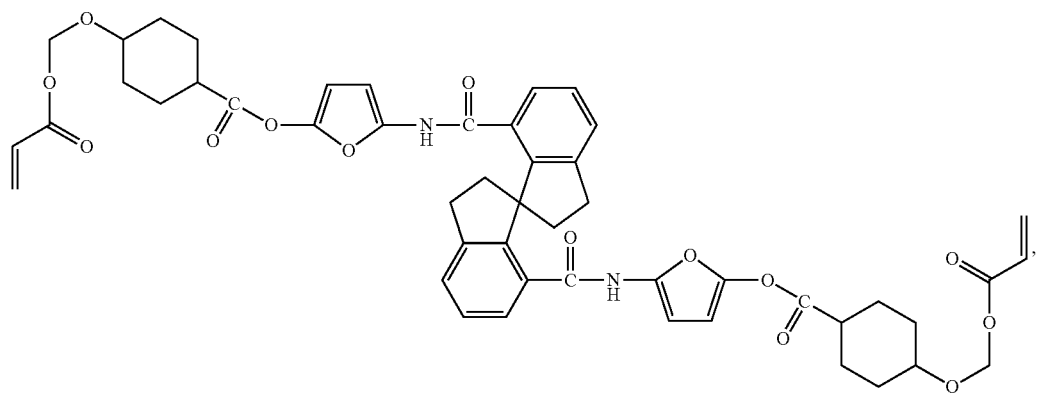
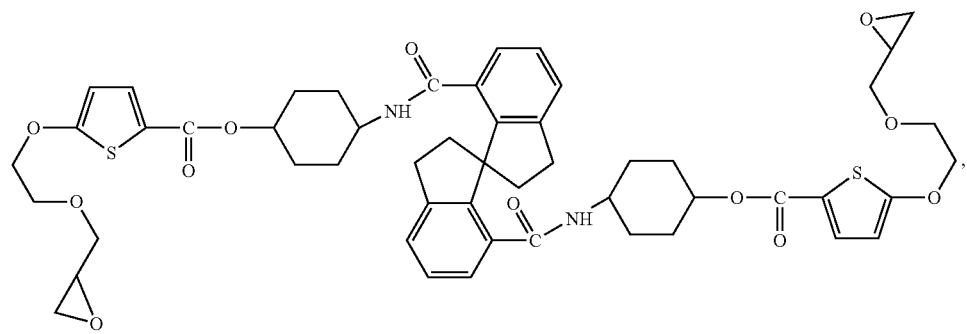
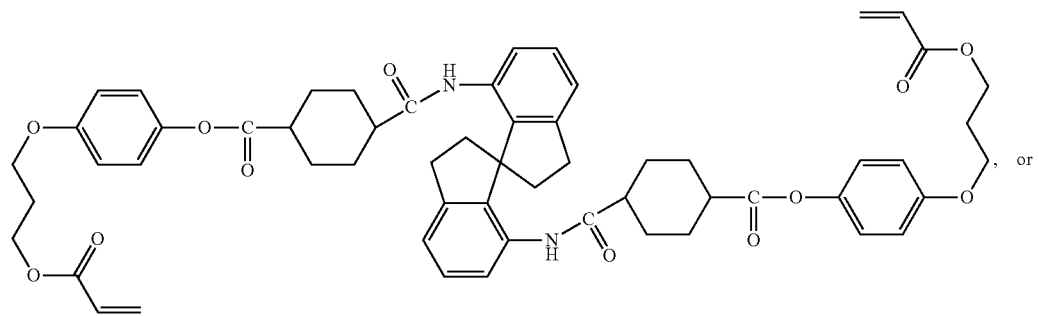
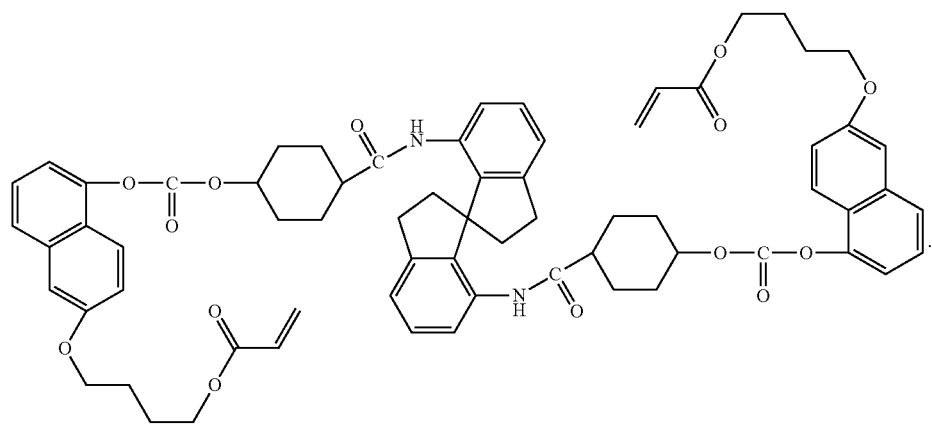

The biindane moiety of the compound represented by Formula (IV) or Formula (V) can be S-form or R-form.

According to other embodiments of the disclosure, the compound of the disclosure can have a structure of Formula (VI) or (VII):

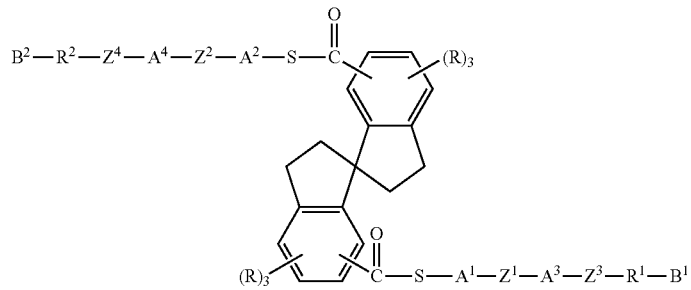

Formula (VI)

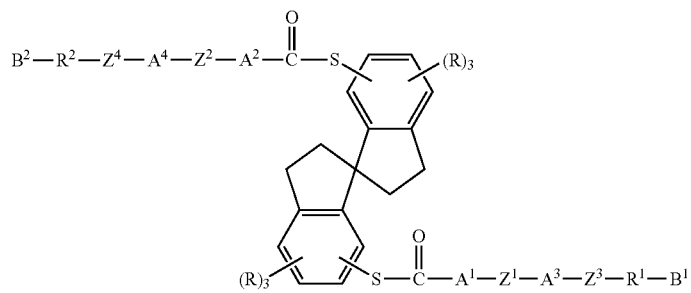

Formula (VII)

wherein $A^1$, $A^2$, $A^3$, $A^4$, $Z^1$, $Z^2$, $Z^3$, $Z^4$, R, $R^1$, $R^2$, $B^1$, and $B^2$ are as previously defined. For example, the compound can be

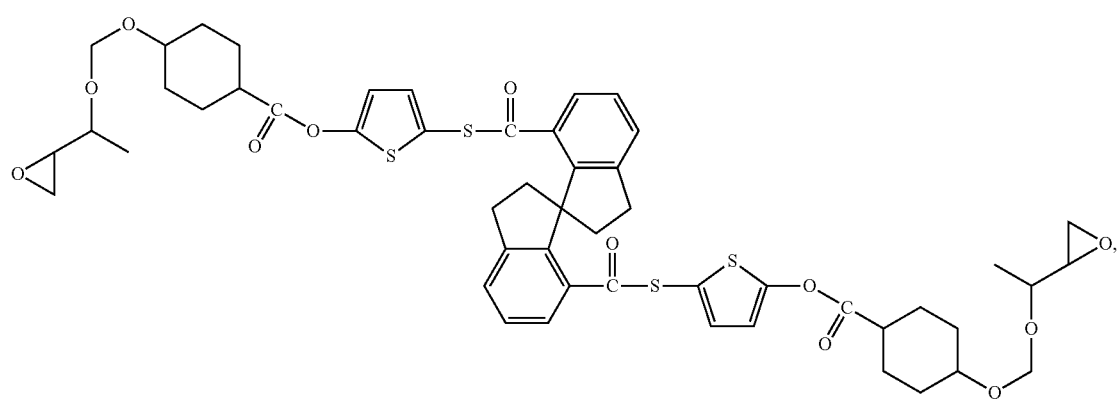

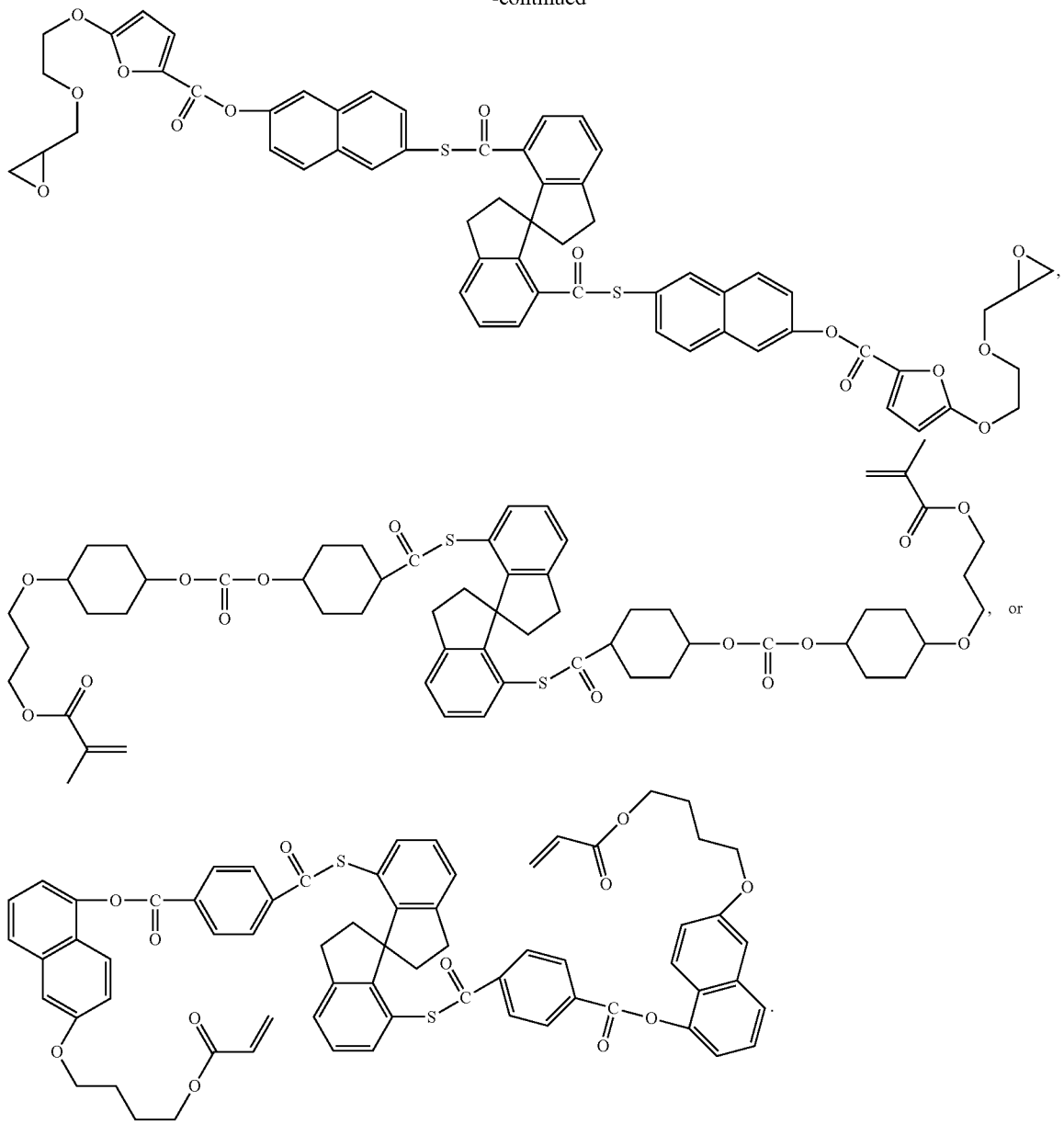

The biindane moiety of the compound represented by Formula (VI) or Formula (VII) can be S-form or R-form.

According to embodiments of the disclosure, the disclosure provides a liquid-crystal composition. The liquid-crystal composition includes (a) 100 parts by weight of a liquid-crystal host; and (b) 0.1-50 parts by weight of a compound having Formula (I). For example, the compound having Formula (I) is present in an amount from 0.1 to 30 parts by weight or from 0.1 to 25 parts by weight.

The compound of the disclosure can serve as a chiral additive and add into nematic liquid-crystal, smectic liquid-crystal, or discotic liquid-crystal. In one embodiment, the compound of the disclosure can mix with nematic liquid-crystal to form a cholesteric liquid-crystal composition used in phototunable liquid-crystal display devices.

The liquid-crystal host can be a compound with or without a polymerizable group. In addition, the liquid-crystal composition of the disclosure can optionally include a polymerizable monomer, a polymerization initiator, a binder resin, a solvent, a surfactant, a tackifying agent, a polymerization inhibitor, an ultraviolet absorber, or other chiral additives. According to embodiments of the disclosure, the polymerizable monomer can be a compound with unsaturated double bond such as: pentaerythritol tetraacrylate, dipentaerythritol hexaacrylate, or derivatives thereof. The polymerization initiator can be p-methoxyphenyl-2,4-bis (trichloromethyl)-s-triazine, 4,4'-bis(N,N-dimethylamino) benzophenone, benzyldimethylketal, or thioxanthone amine. The binder resin can be polystyrene compound (such as polystyrene, or poly-α-methyl styrene), cellulose resins (such as methyl cellulose, ethyl cellulose, or acetyl cellulose), or acetal resin (such as polyvinyl formal, or polyvinyl butyral). The surfactant can be a nonionic surfactant. In order to increase the storability of the liquid-crystal composition, the liquid-crystal composition can include the polymerization inhibitor. The polymerization inhibitor can be hydroquinone, hydroquinone monomethyl ether, phenothiazine, or benzoquinone. The solvent can be 2-butanone, cyclohexanone, dichloromethane, or chloroform Next, 200 mL of methanol was added, and then a solid was deposited. After removing the solid by filtration, the filtrate was collected. After concentration, Compound 2 (maroon liquid) was obtained with a yield of 55%. The synthesis pathway of the above reaction was as follows:

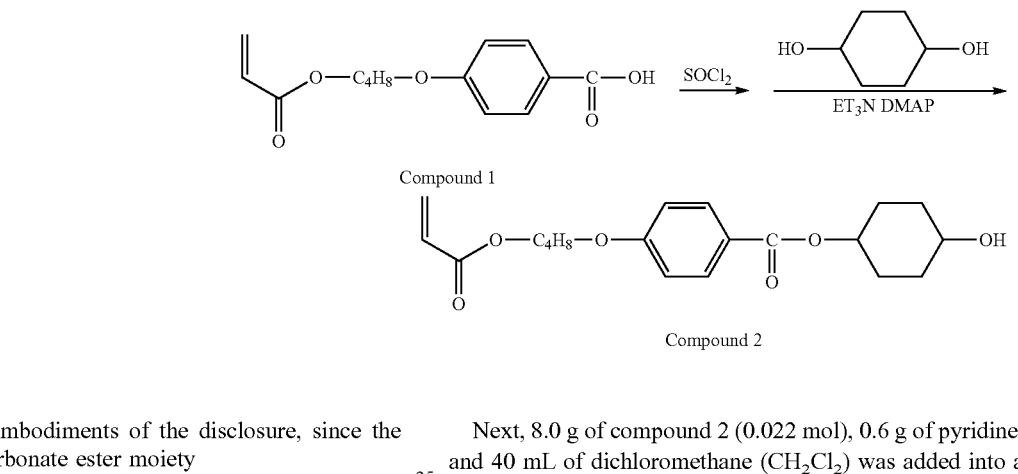

Compound 1

Compound 2

According to embodiments of the disclosure, since the compound has carbonate ester moiety

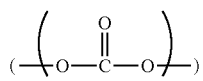

for bonding a side chain, the compound can exhibit high helical twisting power (HTP), improved voltage holding ratio, high solubility in the liquid-crystal host, and long precipitation time under low temperature.

Below, exemplary embodiments will be described in detail so as to be easily realized by a person having ordinary knowledge in the art.

Preparation of Compound

EXAMPLE 1

10 g of Compound 1 (0.038 mol) was added into a reaction bottle. Next, 20 mL of thionyl chloride ($SOCl_2$) was added into the reaction bottle, and the reaction bottle was heated to reflux at 80° C. After Compound 1 was completely dissolved in thionyl chloride, the reaction bottle was still heated to reflux for 30 minutes. Next, after cooling to room temperature (25), thionyl chloride ($SOCl_2$) was removed completely. 40 mL of tetrahydrofuran (THF) was added into the reaction bottle in an ice bath (0° C.), obtaining a first solution. Next, 8.88 g of 1,4-cyclohexanediol (0.076 mol), 7.68 g of triethylamine (0.076 mol), 0.93 g of 4-dimethylaminopyridine (DMAP) (0.0076 mo , and 50 mL of tetrahydrofuran (THF) were added into another reaction bottle, obtaining a second solution. Next, the first solution was added dropwisely into the second solution in an ice bath (0° C.). After the addition was complete, the mixture was stirred in an ice bath (0° C.) for 30 minutes, and then stirred at room temperature (25° C.) for 1 hour. Next, after removing tetrahydrofuran (THF), 100 mL of dichloromethane ($CH_2Cl_2$) was added. After subjecting it to an ultrasonic vibration treatment for 30 minutes, 50 mL of hydrochloric acid aqueous solution (5 wt %) was mixed with the mixture. After extraction, an organic phase was separated, and then dried by anhydrous magnesium sulfate. After concentration, the result was dissolved in 10 mL of tetrahydrofuran (THF).

Next, 8.0 g of compound 2 (0.022 mol), 0.6 g of pyridine, and 40 mL of dichloromethane ($CH_2Cl_2$) was added into a reaction bottle. Next, 2 g of triphosgene (dissolved in 10 mL of dichloromethane) was added slowly into the reaction bottle in an ice bath (0° C.). After stirring for 1 hour, a third solution was obtained. Next, 1.5 g of compound 3 (

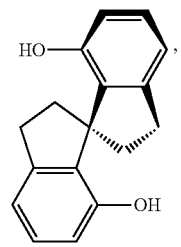

S-form) (0.006 mol), 0.6 g of triethylamine (0.006 mol), 0.01 g of 4-dimethylaminopyridine (DMAP) (0.0006 mol), and 50 mL of tetrahydrofuran (THF) was added into another reaction bottle, obtaining a fourth solution. Next, the third solution was added dropwisely into the fourth solution in an ice bath (0° C.). After the addition was complete, the mixture was stirred in an ice bath (0° C.) for 30 minutes and then stirred at room temperature (25° C.) for 1 hour. Next, after removing tetrahydrofuran (THF), 100 mL of dichloromethane ($CH_2Cl_2$) was added. After subjecting it to an ultrasonic vibration treatment for 30 minutes, 50 mL of hydrochloric acid aqueous solution (5 wt %) was added. After extraction, an organic phase was separated, and then dried by anhydrous magnesium sulfate. After concentration, 10 mL of tetrahydrofuran (THF) was added. Next, 200 mL of methanol was added, and then a solid was deposited. After removing the solid by filtration, the filtrate was collected. After concentration, Chiral Compound 1 was obtained with a yield of 51%. The synthesis pathway of the above reaction was as follows:

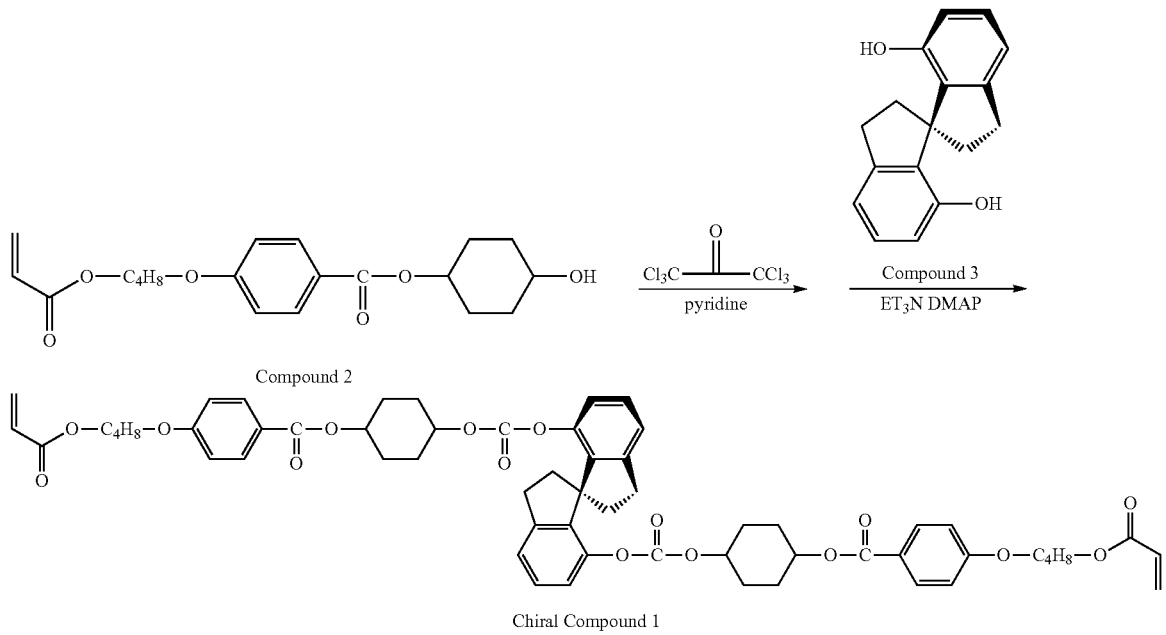

Chiral Compound 1 was analyzed by nuclear magnetic resonance (NMR) spectroscopy and the result is as follows: $^1$H NMR (300 MHz, CDCl$_3$): 1.27-1.31(m, 8H), 1.43(s, 8H), 1.91(s 8H), 2.30-2.38(m,4H), 3.1(d, J=2.75 Hz, 4H),4.06(d, J=4.4 Hz, 4H), 4.25-4.27(d, J=5.6 Hz, 4H) 4.52(m,2H), 5.02(m, 2H), 5.83-5.85(d, J=10.3 Hz, 2H), 6.11-6.16(dd, J=8.4,10.4 Hz 2H), 6.40-6.44(d, J=17.34 Hz, 2H), 6.90-6.92 (d, J=8.6 Hz, 4H), 7.00-7.02(d, J=7.9 Hz, 2H), 7.15-7.17(d, J=8.1 Hz, 2H), 7.23-7.25(d, J=8.0 Hz, 2H), 7.97-7.98(d, J=8.5Hz, 4H)

EXAMPLE 2

10 g of compound 1 (0.038 mol) was added into a reaction bottle. Next, 20 mL of thionyl chloride (SOCl$_2$) was added into the reaction bottle, and the reaction bottle was heated to reflux at 80° C. . After Compound 1 was completely dissolved in thionyl chloride, the reaction bottle was still heated to reflux for 30 minutes. Next, after cooling to room temperature (25), thionyl chloride (SOCl$_2$) was removed completely. 40 mL of tetrahydrofuran (THF) was added into the reaction bottle in an ice bath (0° C.), obtaining a first solution. Next, 8.33 g of hydroquinone (0.076 mol), 7.68 g of triethylamine (0.076 mol), 0.93 g of 4-dimethylaminopyridine, (DMAP) (0.0076 mol), and 50 mL of tetrahydrofuran (THF) were added into another reaction bottle, obtaining a second solution. Next, the first solution was added dropwisely into the second solution in an ice bath (0° C.). After the addition was complete, the mixture was stirred at in an ice bath (0° C.) for 30 minutes, and then stirred at room temperature (25° C.) for 1 hour. Next, after removing tetrahydrofuran (THF), 100 mL of dichloromethane (CH$_2$Cl$_2$) was added. After subjecting it to an ultrasonic vibration treatment for 30 minutes, 50 mL of hydrochloric acid aqueous solution (5 wt %) was mixed with the mixture. After extraction, an organic phase was separated, and then dried by anhydrous magnesium sulfate. After concentration, the result was dissolved in 10 mL of tetrahydrofuran (THF). Next, 200 mL of methanol was added, and then a solid was deposited. After removing the solid by filtration, the filtrate was collected. After concentration, Compound 4 (maroon liquid) was obtained with a yield of 56%. The synthesis pathway of the above reaction was as follows:

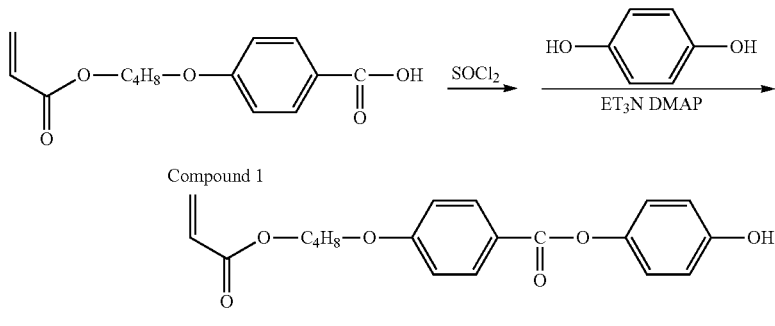

Next, 5.3 g of compound 4(0.015 mol), 0.6 g of pyridine, and 40 mL of dichloromethane (CH$_2$Cl$_2$) were added into a reaction bottle. Next, 2 g of triphosgene (dissolved in 10 mL of dichloromethane) was added slowly into the reaction bottle in an ice bath (0° C.). After stirring for 1 hour, a third solution was obtained. Next, 1.5 g of compound 3(

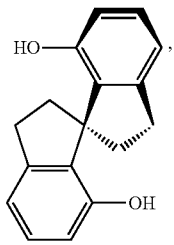

S-form) (0.006 mol), 0.6 g of triethylamine (0.006 mol), 0.01 g of 4-dimethylaminopyridine (DMAP) (0.0006 mol), and 50 mL of tetrahydrofuran (THF) were added into another reaction bottle, obtaining a fourth solution. Next, the third solution was added dropwisely into the fourth solution in an ice bath (0° C.). After the addition was complete, the mixture was stirred in an ice bath (0° C.) for 30 minutes and then stirred at room temperature (25° C.) for 1 hour. Next, after removing tetrahydrofuran (THF), 100 mL of dichloromethane ($CH_2Cl_2$) was added. After subjecting it to an ultrasonic vibration treatment for 30 minutes, 50 mL of hydrochloric acid aqueous solution (5 wt %) was added. After extraction, an organic phase was separated, and then dried by anhydrous magnesium sulfate. After concentration, 10 mL of tetrahydrofuran (THF) was added. Next, 200 mL of methanol was added, and then a solid was deposited. After removing the solid by filtration, the filtrate was collected. After concentration, Chiral Compound 2 was obtained with a yield of 75%. The synthesis pathway of the above reaction was as follows:

Chiral Compound 2 was analyzed by nuclear magnetic resonance (NMR) spectroscopy and the result is as follows: $^1$H NMR (300 MHz, $CDCl_3$): 1.95(s, 8H), 2.33-2.41(m,4H), 3.3(d, J=2.75 Hz,4H), 4.01(d, J=4.4 Hz, 4H), 4.21-4.24(d, J=5.5 Hz, 4H), 5.80-5.83(d, J=10.1 Hz, 2H), 6.11-6.16(dd, J=8.4,10.4 Hz, 2H), 6.40-6.44(d, J=17.34 Hz, 2H), 6.90-6.92(d, J=8.6 Hz, 4H),6.96-6.99(d, J=8.8 Hz, 4H), 7.00-7.02 (d, J=7.9 Hz, 2H), 7.02-7.04(d, J=8.8 Hz, 4H), 7.15-7.17(d, J=8.1 Hz, 2H), 7.23-7.25(d, J=8.0 Hz, 2H), 7.97-7.98(d, J=8.5 Hz, 4H)

The helical twisting power (HTP) of Chiral Compound 1(prepared by Example 1) and Chiral Compound 2 (prepared by Example 2) were measured, and the result was shown in Table 1.

TABLE 1

|  | Chiral Compound 1 | Chiral Compound 2 |
| --- | --- | --- |
| HTP ($\mu m^{-1}$) | 45 | 85 |

As shown in Table 1, since the compound represented by Formula (I) of the disclosure exhibits higher helical twisting power, a reduced dosage of the chiral compound can be employed by the liquid-crystal composition for achieving a predetermined pitch, resulting in reducing the driving voltage and cost of the liquid-crystal device and preventing the characteristics and phase behavior of the liquid-crystal composition from deteriorating.

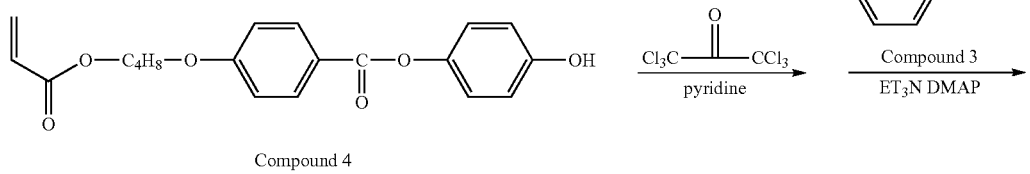

Compound 4

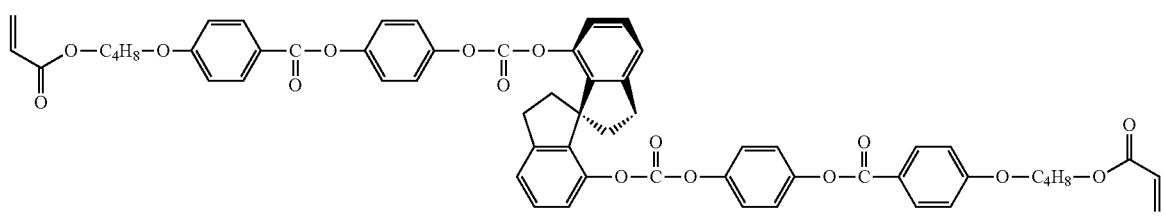

Chiral Compound 2

EXAMPLE 3

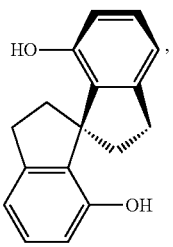

1 g of compound 3(S-form) (0.004 mol), 0.4 g of triethylamine (0.076 mol), 4 g of 4-nitrophenyl chloroformate (0.02 mol), and 10 ml of tetrahydrofuran (THF) were added into a reaction bottle. After stirring at 25° C. for 48 hrs, tetrahydrofuran (THF) was removed and then 10 mL of ethyl acetate (EA) and 10 ml of water were added into the reaction bottle. After extraction, an organic phase was separated, and then dried by anhydrous magnesium sulfate. After concentration and recrystallization with tetrahydrofuran (THF) and methanol, Chiral Compound 3 was obtained with a yield of 50%. The synthesis pathway of the above reaction was as follows:

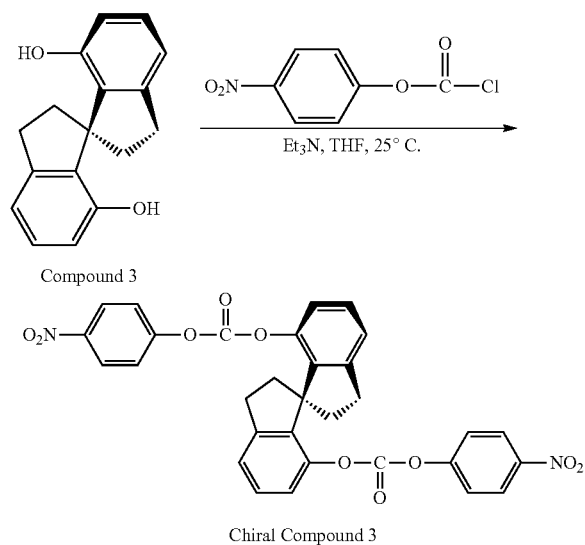

Chiral Compound 3 was analyzed by nuclear magnetic resonance (NMR) spectroscopy and the result is as follows:
$^1$H NMR (400 MHz, CDCl$_3$): 2.33-2.38(m,2H),2.45-2.50 (m,2H),3.10-3.20(m,4H),7.08-7.10(d, J=7.2 Hz 4H), 7.13-7.15(d, J=6.4 Hz 2H), 7.18-7.20(d, J=5.6 Hz 2H), 7.25-7.27 (d, J=6.0 Hz 2H), 8.17-8.19(d, J=7.2 Hz 4H)
Characteristics of liquid-crystal composition

EXAMPLE 4

0.01 g of Chiral Compound 1 was mixed with 4.99 g negative liquid-crystal host (Δn=0.1, Δε=−2.1, having a viscosity of 20 mPa·s), obtaining a liquid-crystal composition. The voltage holding ratio (VHR) and precipitation time under low temperature of the liquid-crystal composition were measured, and the results were shown in Table 2.

TABLE 2

| | weight ratio of Chiral Compound 1 | voltage holding ratio | precipitation time under low temperature | |
|---|---|---|---|---|
| | (wt %) | (VHR) | −40° C. | −25° C. |
| Chiral Compound 1 | 0.2 wt % | 98% | 4 weeks | 4 weeks |

As shown in Table 2, the liquid-crystal composition employing the compound of the disclosure exhibits high voltage holding ratio (≥95%), resulting in improving the image contrast and reducing the image sticking of the active matrix liquid-crystal display device employing the liquid-crystal composition. Furthermore, the compound of the disclosure has long precipitation time under low temperature (such as −25° C. or −40° C.).

EXAMPLE 5

Solubility (wt %)
Chiral Compound 1 and Chiral Compound 2 were mixed with the liquid-crystal host (with a trade No. of IBL-087) individually for measuring the maximum additive weight percentage of Chiral Compound 1 (or Chiral Compound 2), wherein the maximum additive concentration was determined by whether the Chiral Compound was precipitated on the sidewall of the bottle. The results are shown in Table 3.

| | Chiral Compound 1 | Chiral Compound 2 |
|---|---|---|
| solubility (wt %) | 16 wt % | 17 wt % |

As shown in Table 3, the compound of the disclosure has high solubility (>15 wt %) in the liquid-crystal host.

It will be clear that various modifications and variations can be made to the disclosed methods and materials. It is intended that the specification and examples be considered as exemplary only, with the true scope of the disclosure being indicated by the following claims and their equivalents.

What is claimed is:
1. A compound, having Formula (I):

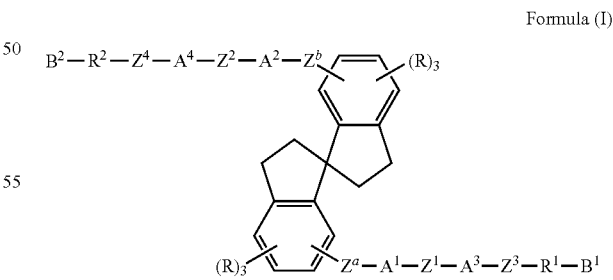

Formula (I)

$Z^a$ and $Z^b$ are independently

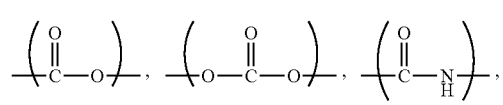

-continued

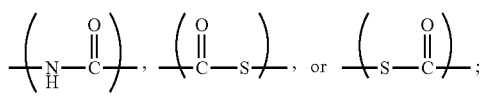

$A^1$ and $A^2$ are independently

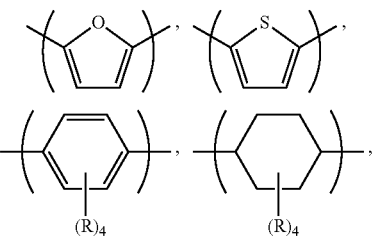

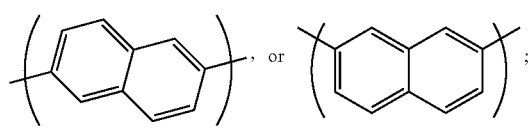

$A^3$ and $A^4$ are independently single bond,

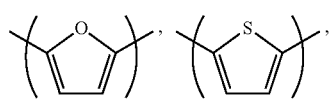

-continued

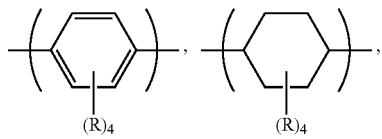

$Z_1$, $Z_2$, $Z_3$, and $Z^4$ are independently single bond,

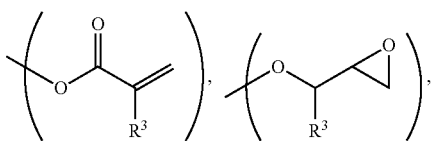

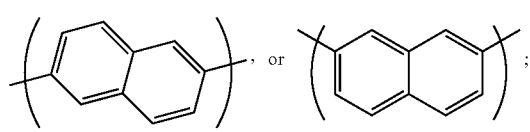

R is independently hydrogen, or $C_{1-4}$ alkyl group; $R^1$ and $R^2$ are independently single bond, —O—$(CH_2)_n$—, —CH=CH—$(CH_2)_2$—, —$(CH_2)_2$—CH=CH—, —CH=CH—, or —C≡C—; n is an integer from 1 to 6; $B^1$ and $B^2$ are independently

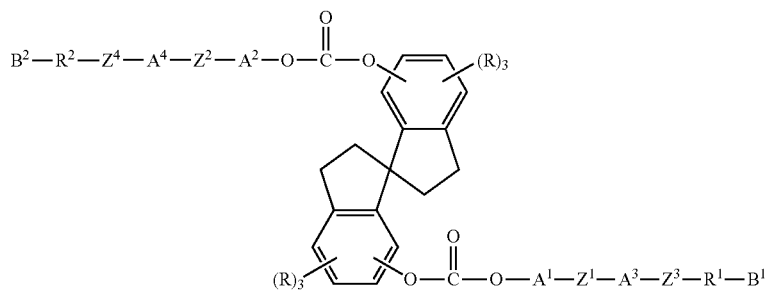

or —$(NO_2)$; and, $R^3$ is hydrogen, or methyl group.

2. The compound as claimed in claim 1, wherein the compound has Formula (II):

Formula (II)

$A^1$ and $A^2$ are independently

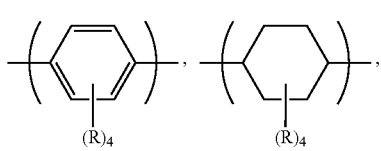

-continued

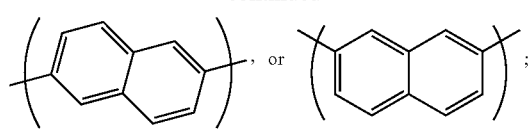

A³ and A⁴ are independently single bond,

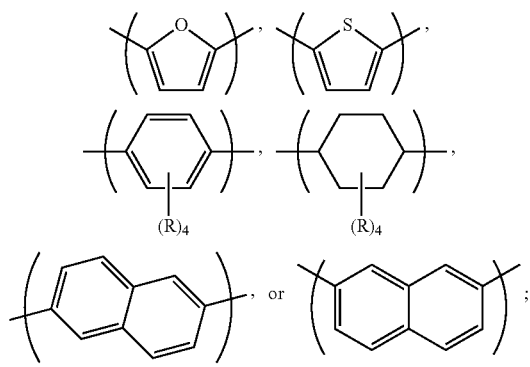

Z¹, Z², Z³, and Z⁴ are independently single bond,

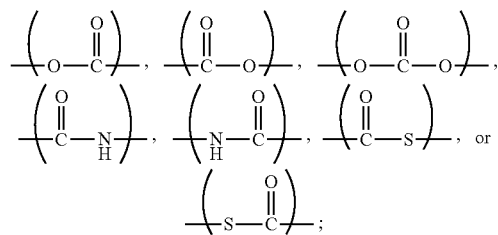

R is independently hydrogen, or $C_{1-4}$ alkyl group; $R^1$ and $R^2$ are independently single bond, —O—(CH$_2$)$_n$—, —CH=CH—(CH$_2$)$_2$—, —(CH$_2$)$_2$—CH=CH—, —CH=CH—, or —C≡C—; n is an integer from 1 to 6; $B^1$ and $B^2$ are independently

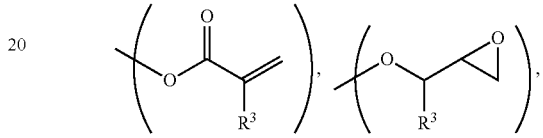

or —(NO$_2$); and, $R^3$ is hydrogen, or methyl group.

3. The compound as claimed in claim 2, wherein the compound is

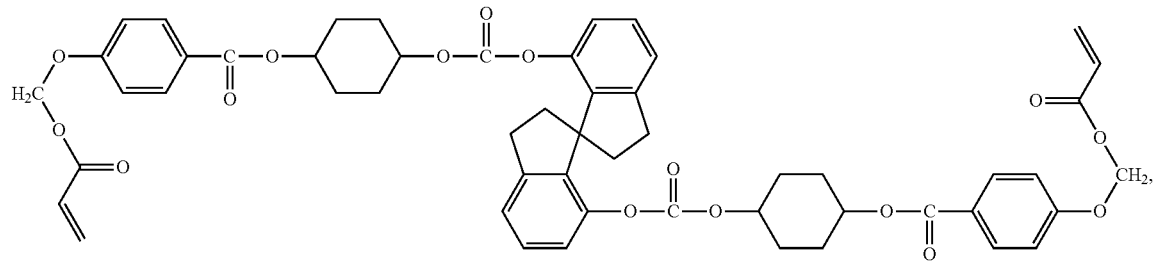

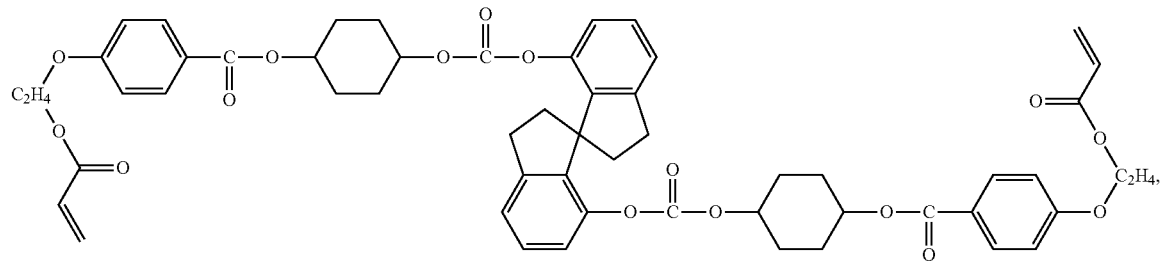

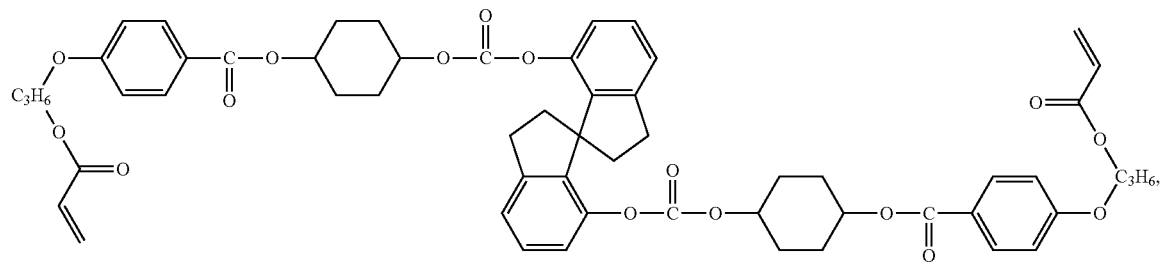

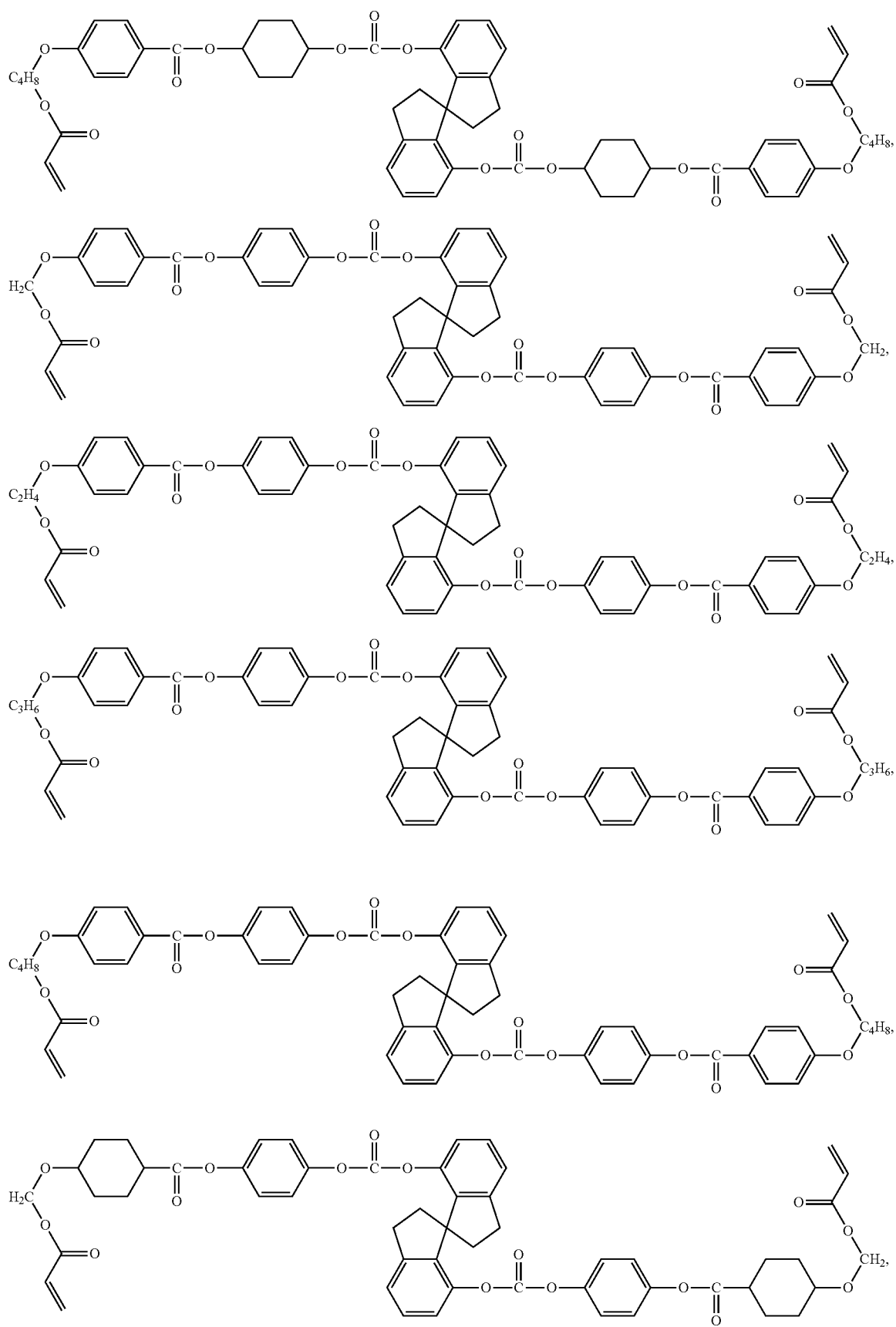

-continued
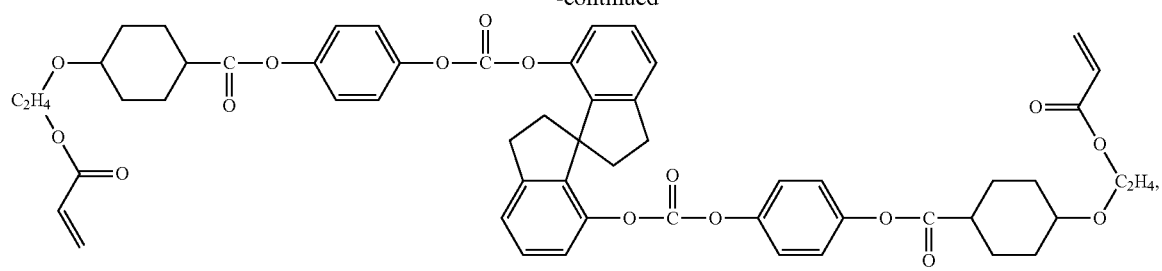
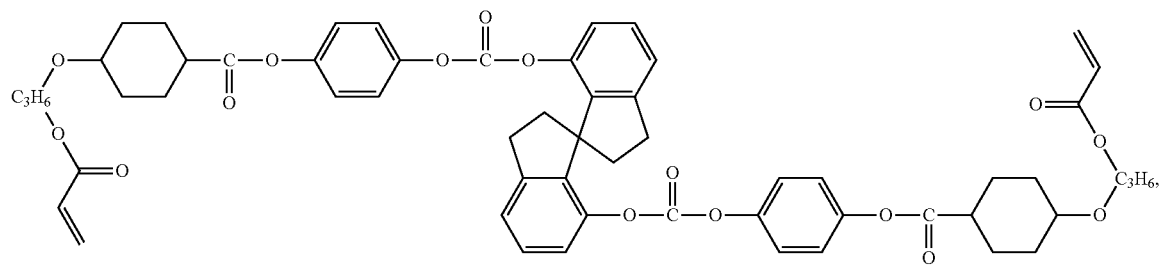
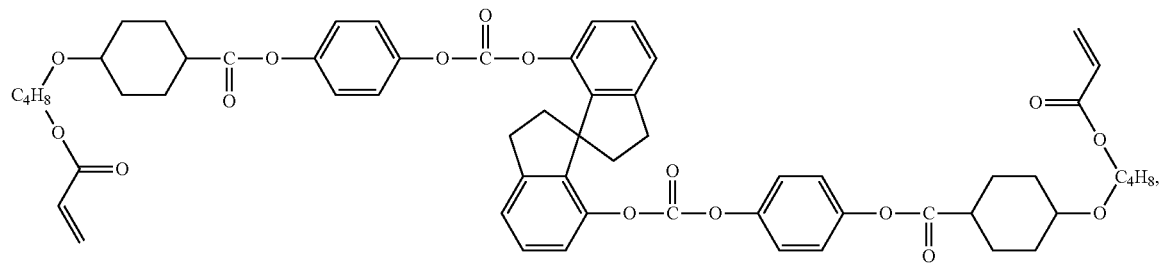
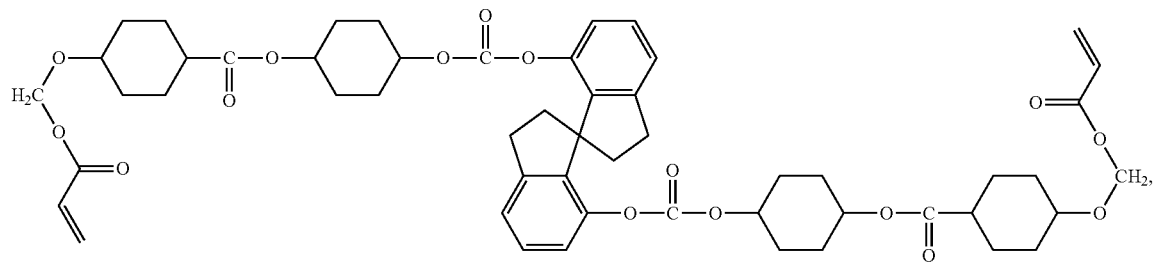
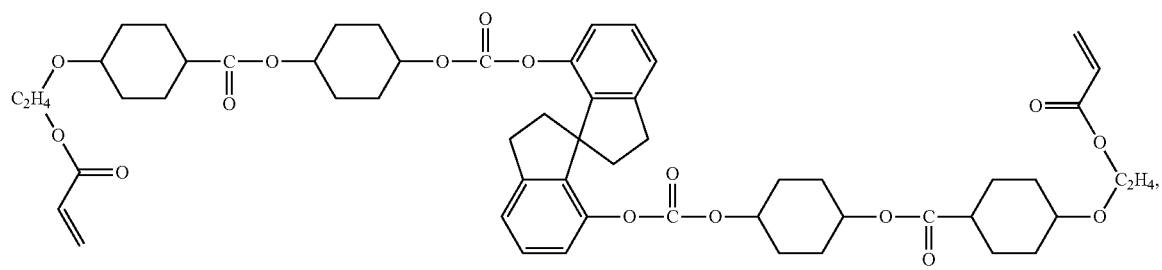
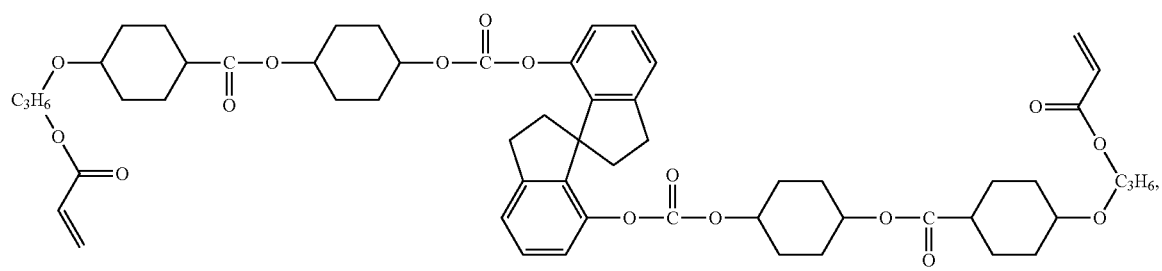

-continued

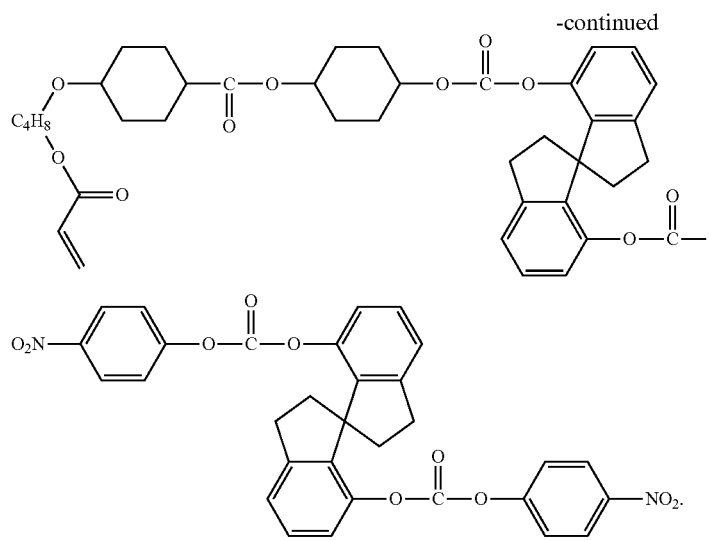
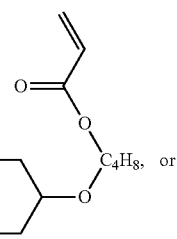

4. The compound as claimed in claim 1, wherein the compound has Formula (III):

Formula (III)

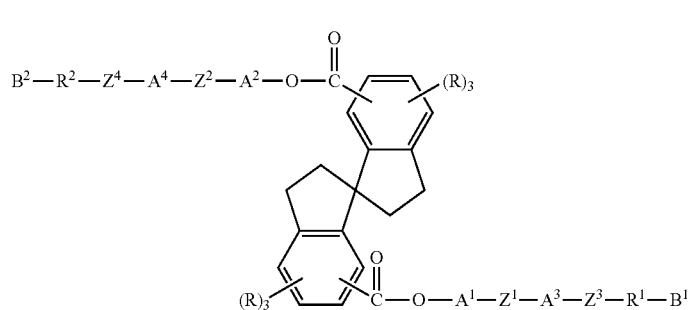

$A^1$ and $A^2$ are independently

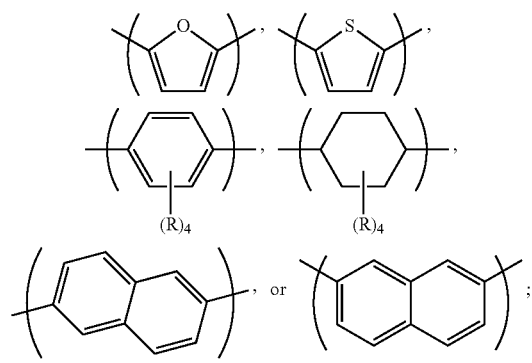

$A^3$ and $A^4$ are independently single bond,

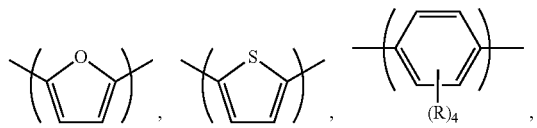

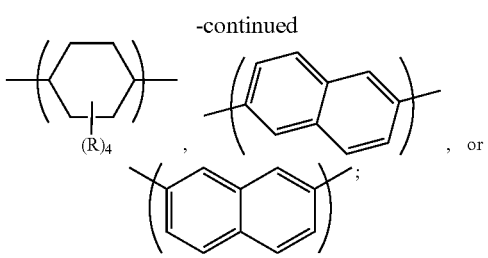

$Z^1$, $Z^2$, $Z^3$, and $Z^4$ are independently single bond,

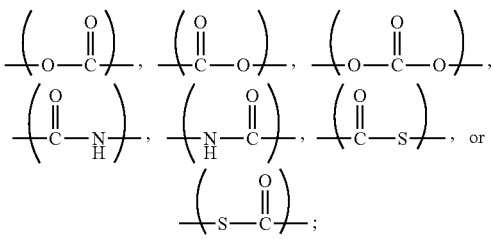

R is independently hydrogen, or $C_{1-4}$ alkyl group; $R^1$ and $R^2$ are independently single bond, $-O-(CH_2)_n-$, $-CH=CH-(CH_2)_2-$, $-(CH_2)_2-CH=CH-$, $-CH=CH-$, or $-C\equiv C-$; n is an integer from 1 to 6; $B^1$ and $B^2$ are independently

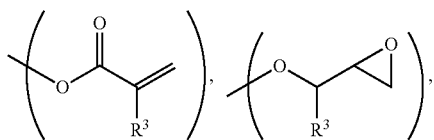
or —(NO$_2$); and, R$^3$ is hydrogen, or methyl group.
5. The compound as claimed in claim 4, wherein the compound is
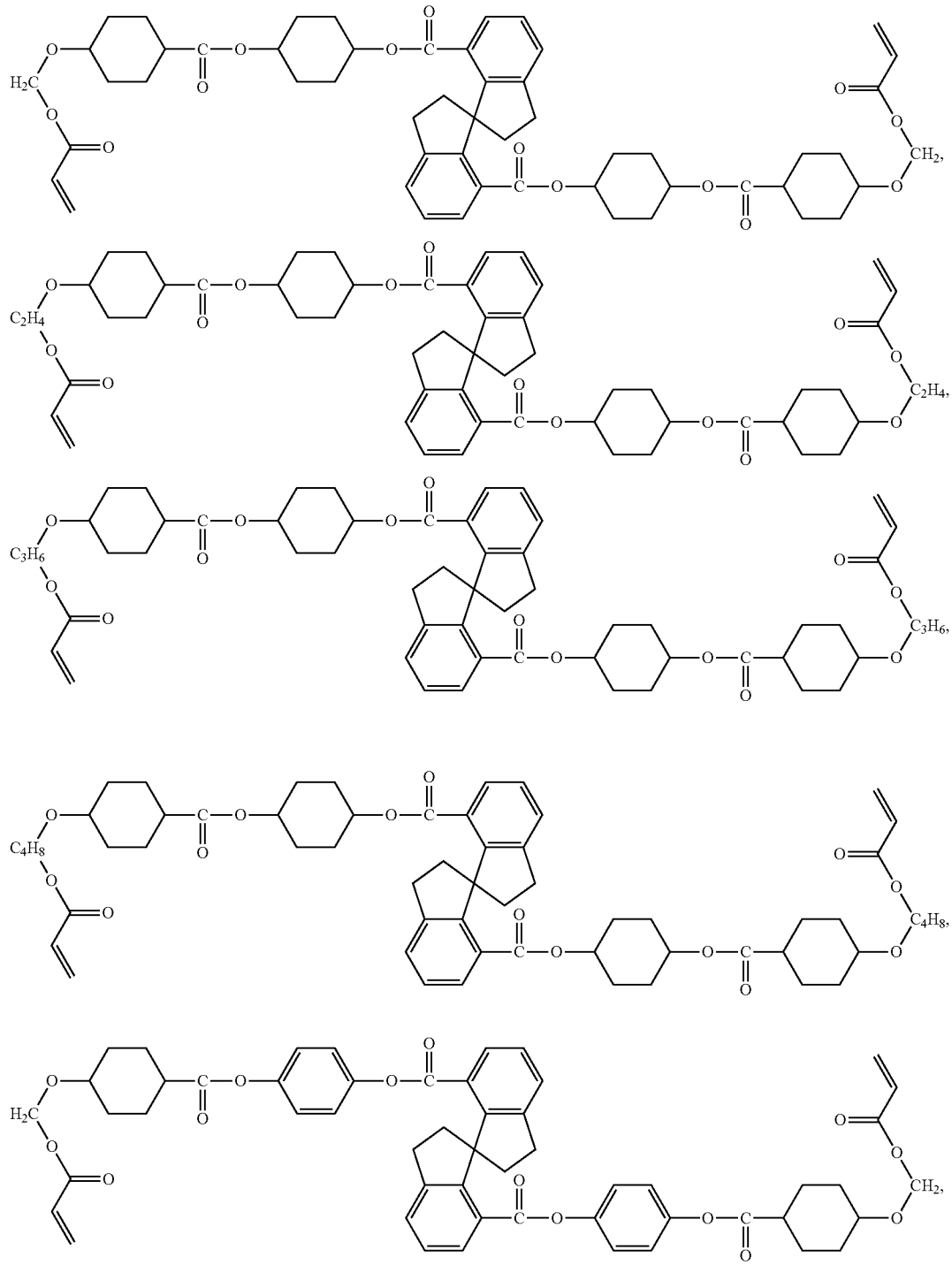

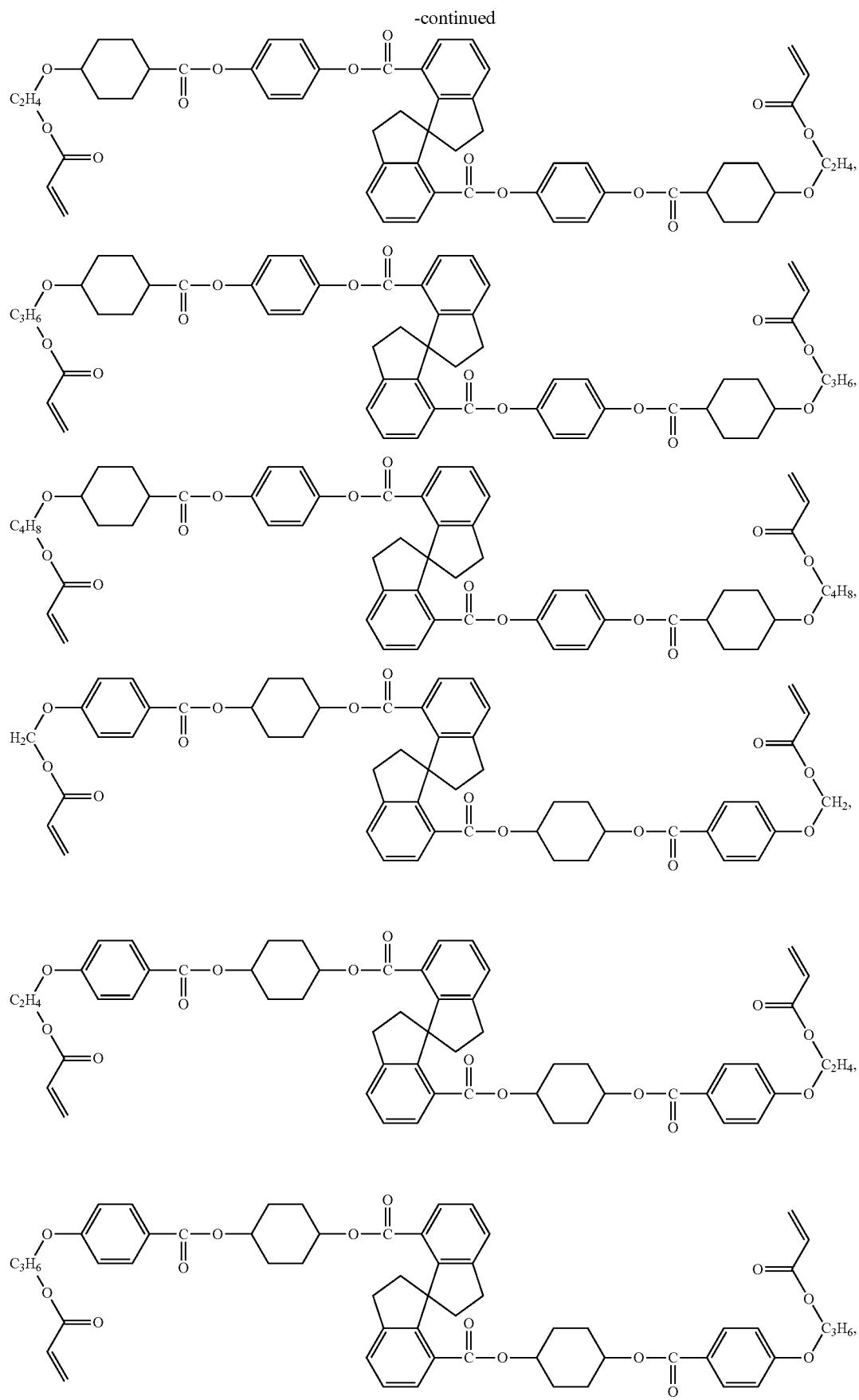

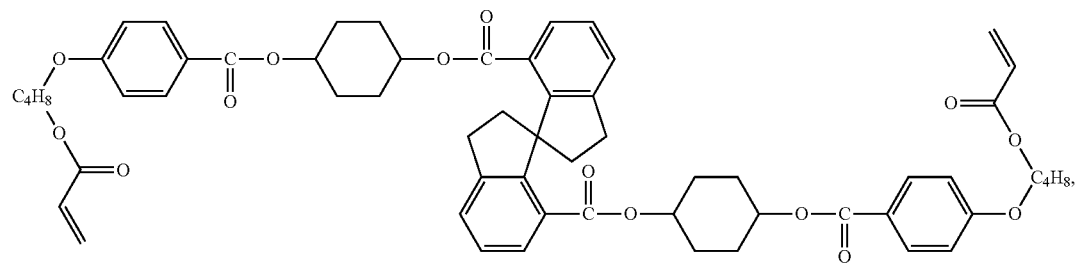
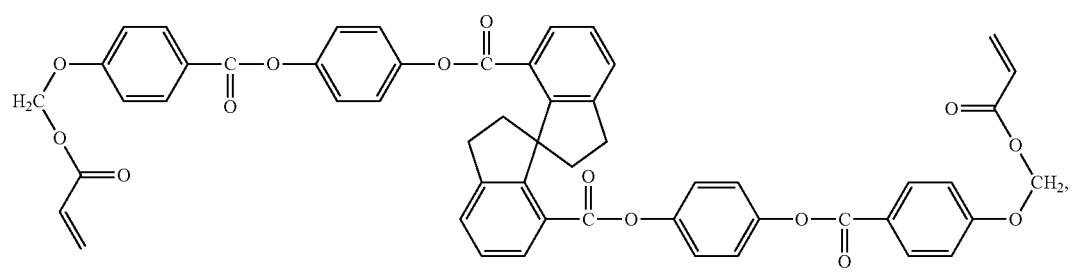
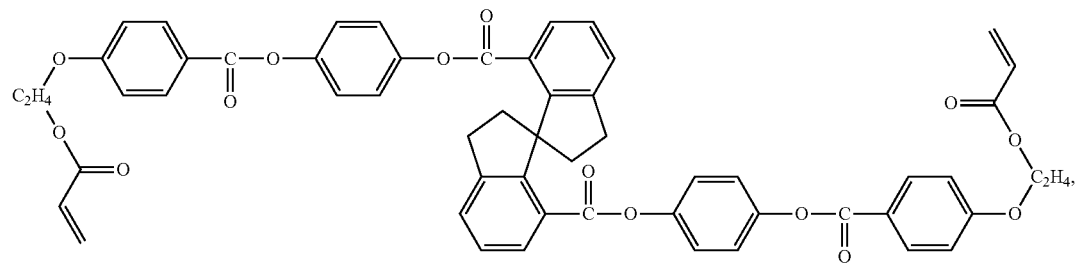
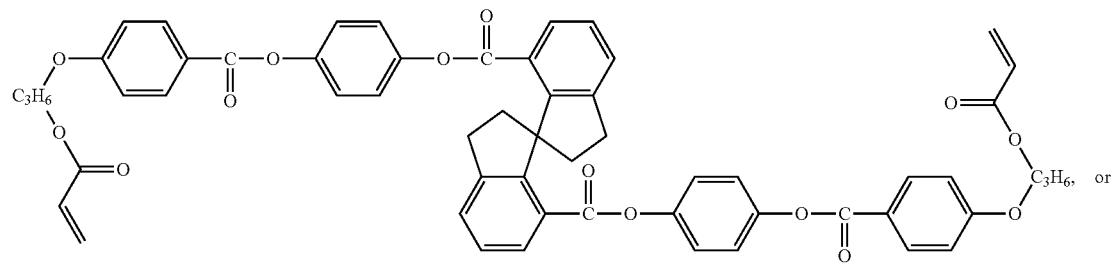
or
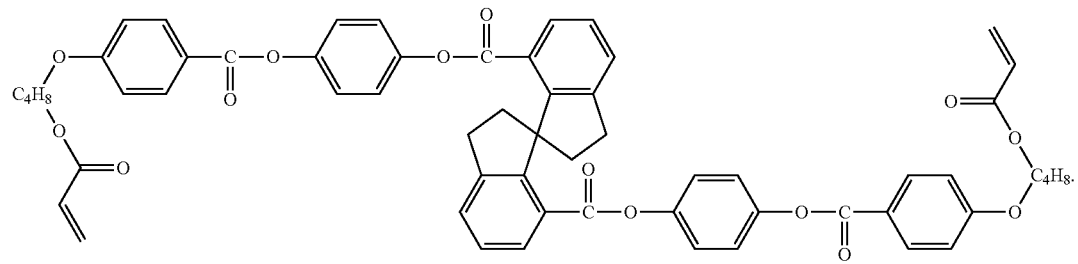

6. The compound as claimed in claim 1, wherein the compound has Formula (IV) or (V):

Formula (IV)

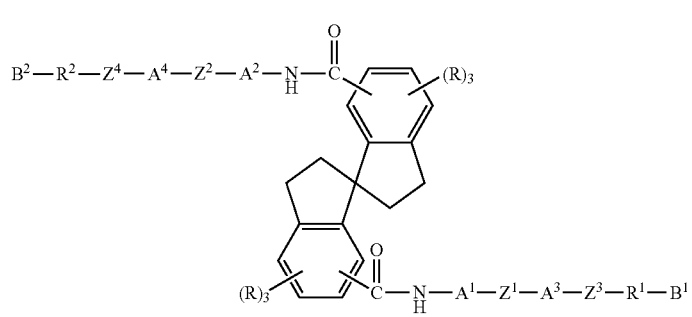

Formula (V)

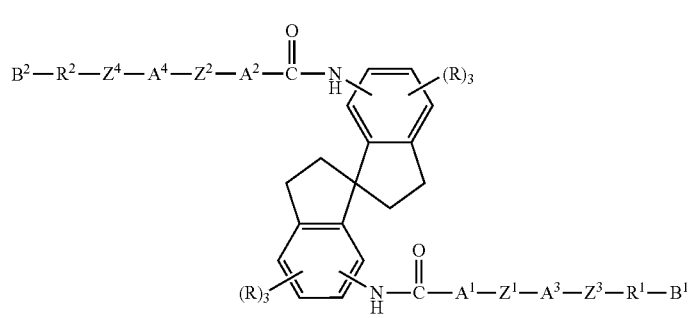

$A^1$ and $A^2$ are independently

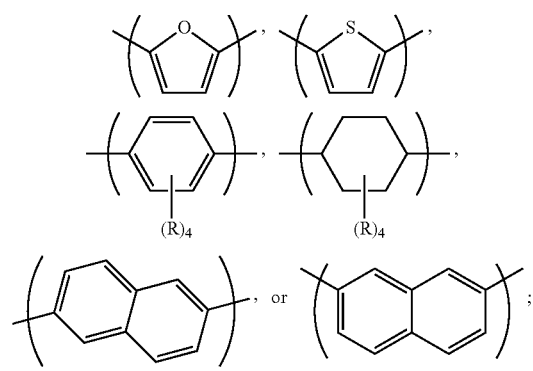

$A^3$ and $A^4$ are independently single bond,

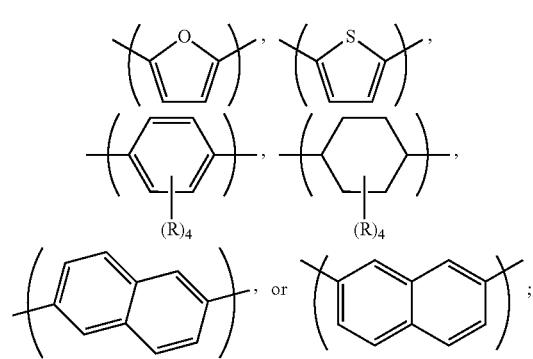

$Z^1$, $Z^2$, $Z^3$, and $Z^4$ are independently single bond, $$-\!\!\left(\!\!O-\overset{\overset{\displaystyle O}{\|}}{C}\!\!\right)\!\!-,\ -\!\!\left(\!\!\overset{\overset{\displaystyle O}{\|}}{C}-O\!\!\right)\!\!-,\ -\!\!\left(\!\!O-\overset{\overset{\displaystyle O}{\|}}{C}-O\!\!\right)\!\!-,$$

$$-\!\!\left(\!\!\overset{\overset{\displaystyle O}{\|}}{C}-\overset{\displaystyle}{\underset{\displaystyle H}{N}}\!\!\right)\!\!-,\ -\!\!\left(\!\!\overset{\displaystyle}{\underset{\displaystyle H}{N}}-\overset{\overset{\displaystyle O}{\|}}{C}\!\!\right)\!\!-,\ -\!\!\left(\!\!\overset{\overset{\displaystyle O}{\|}}{C}-S\!\!\right)\!\!-,\ \text{or}$$

$$-\!\!\left(\!\!S-\overset{\overset{\displaystyle O}{\|}}{C}\!\!\right)\!\!-;$$

R is independently hydrogen, or $C_{1-4}$ alkyl group; $R^1$ and $R^2$ are independently single bond, $-O-(CH_2)_n-$, $-CH=CH-(CH_2)_2-$, $-(CH_2)_2-CH=CH-$, $-CH=CH-$, or $-C\equiv C-$; n is an integer from 1 to 6; $B^1$ and $B^2$ are independently $$\left(\!\!-O-\overset{\overset{\displaystyle O}{\|}}{C}-\overset{\displaystyle}{\underset{\displaystyle R^3}{C}}\!\!=\!CH_2\right),\ \left(\!\!-O-CH-\overset{\displaystyle}{\underset{\displaystyle R^3}{C}}\!\!\begin{array}{c}O\\\diagup\backslash\\CH_2\end{array}\right),$$

or $-(NO_2)$; and, $R^3$ is hydrogen, or methyl group.

7. The compound as claimed in claim 6, wherein the compound is

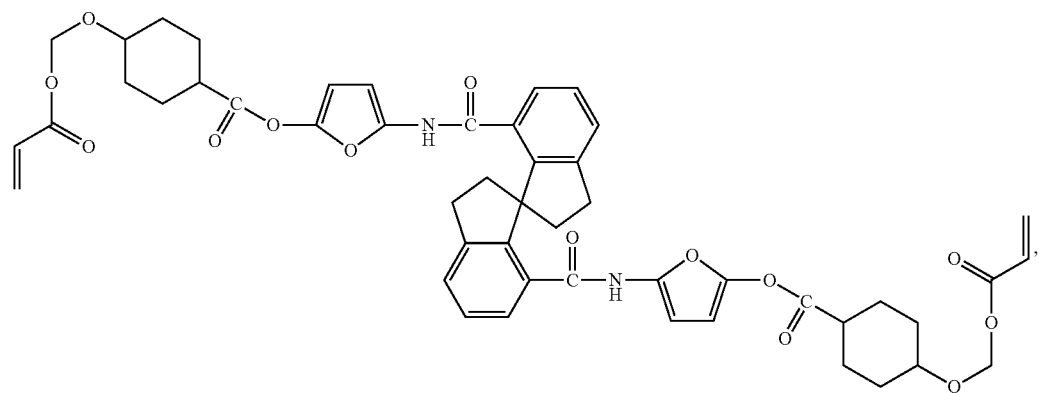
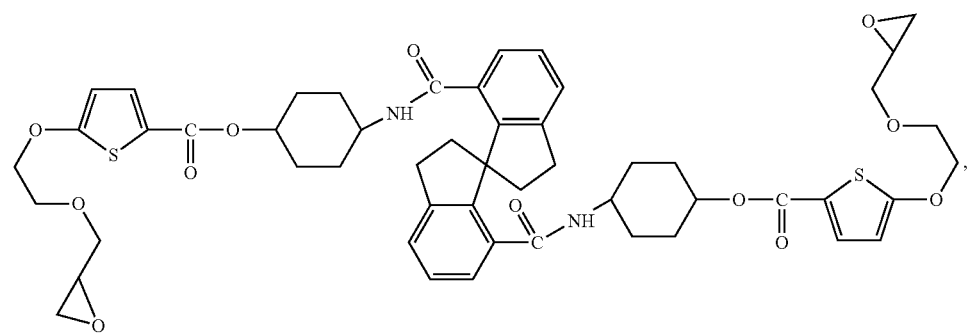
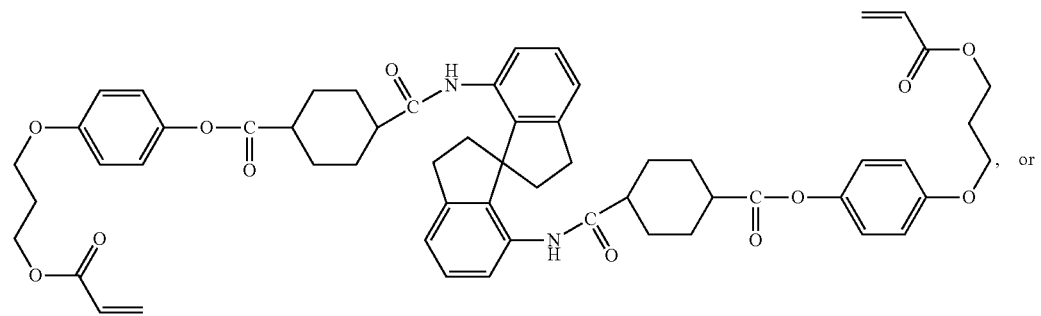
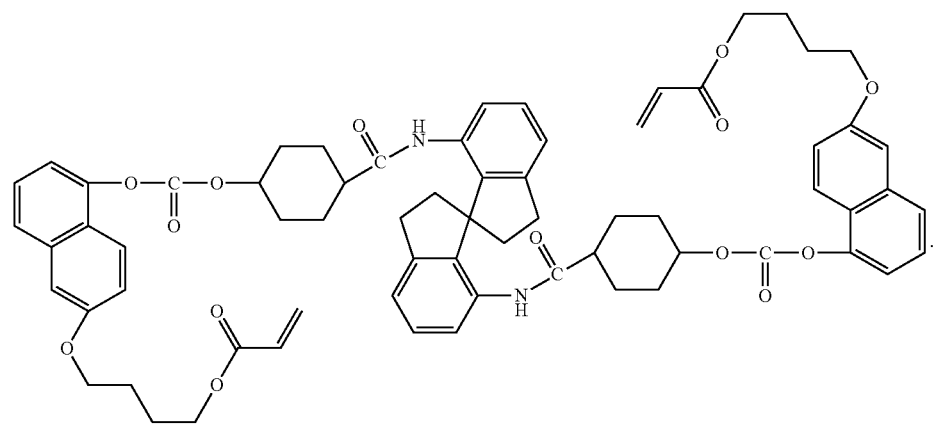

8. The compound as claimed in claim 1, wherein the compound has Formula (VI) or (VII):

Formula (VI)

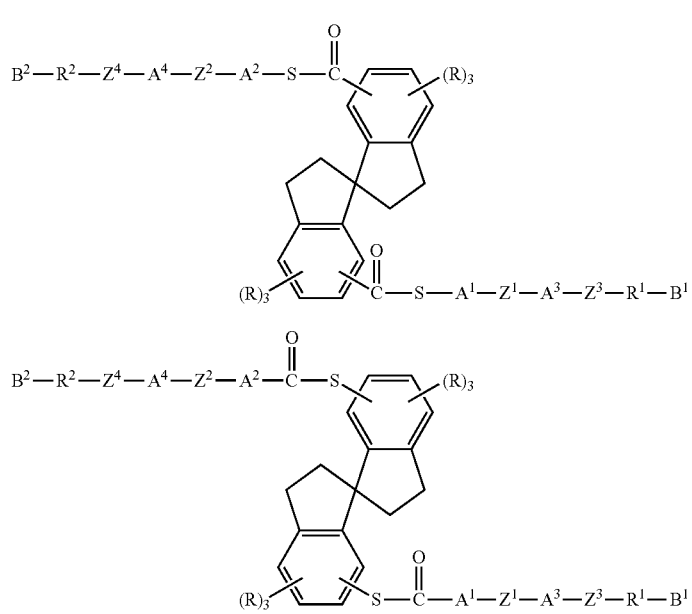

Formula (VII)

$A^1$ and $A^2$ are independently

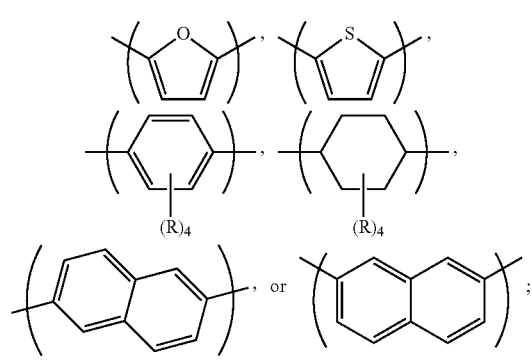

$A^3$ and $A^4$ are independently single bond,

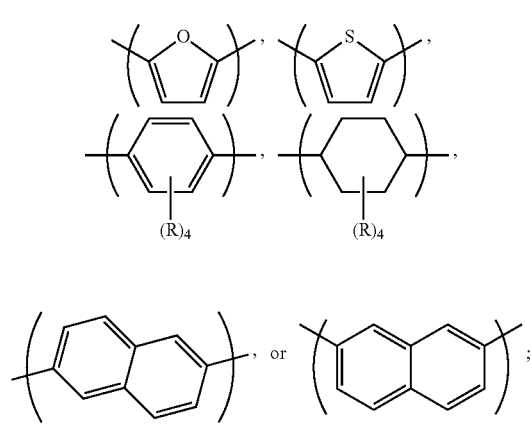

$Z^1$, $Z^2$, $Z^3$, and $Z^4$ are independently single bond,

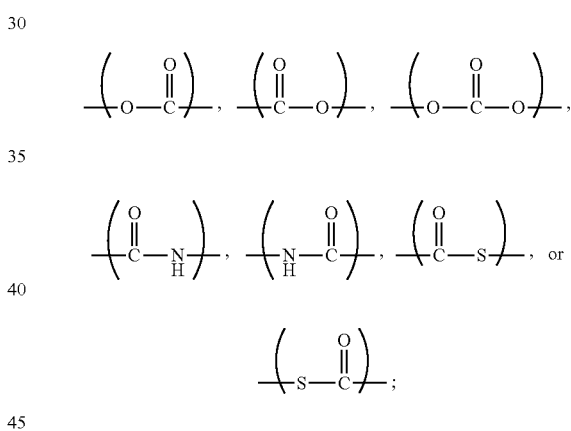

R is independently hydrogen, or $C_{1-4}$ alkyl group; $R^1$ and $R^2$ are independently single bond, —O—$(CH_2)_n$—, —CH=CH—$(CH_2)_2$—, —$(CH_2)_2$—CH=CH—, —CH=CH—, or —C≡C—; n is an integer from 1 to 6; $B^1$ and $B^2$ are independently

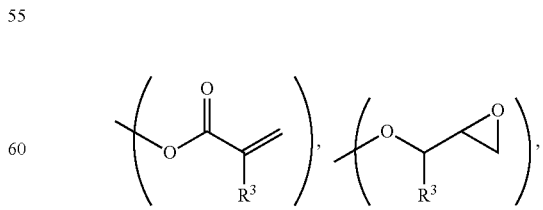

or —($NO_2$); and, $R^3$ is hydrogen, or methyl group.

9. The compound as claimed in claim 8, wherein the compound is

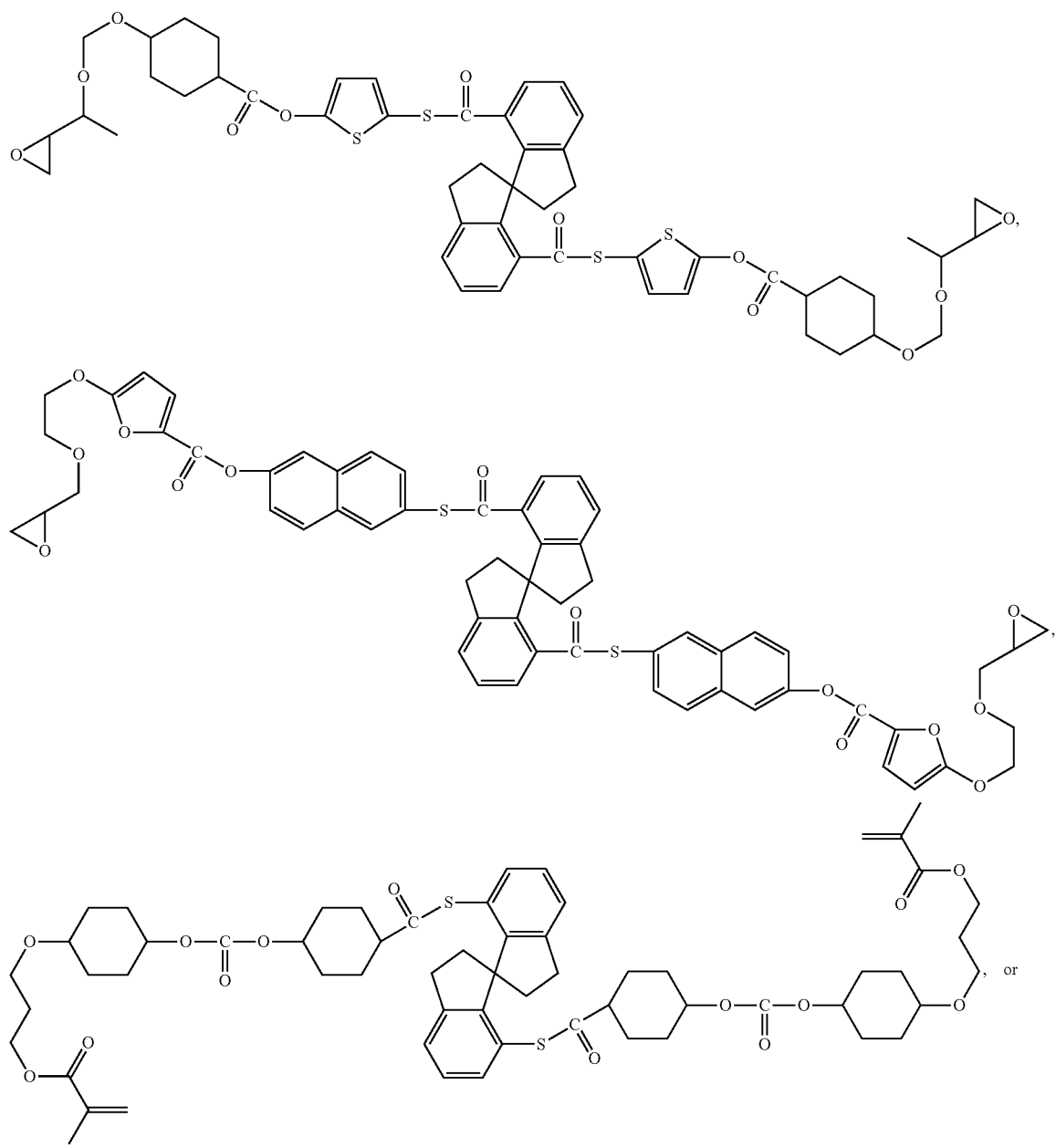
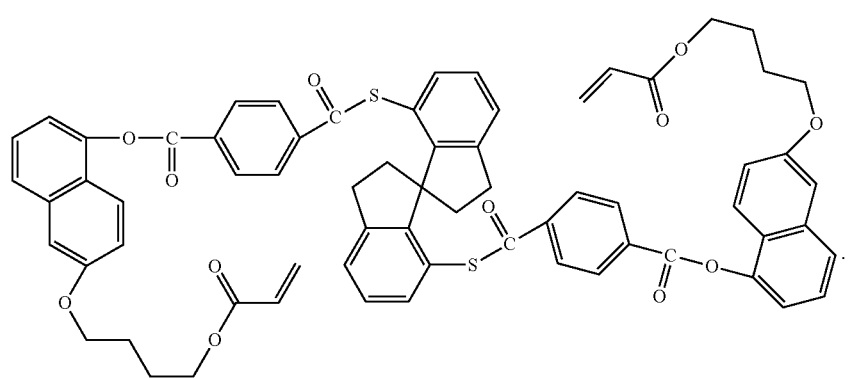

10. A liquid-crystal composition, comprising:
100 parts by weight of liquid-crystal host; and
0.1-30 parts by weight of the compound as claimed in claim 1.

* * * * *